US011246975B2

(12) United States Patent
Locke et al.

(10) Patent No.: US 11,246,975 B2
(45) Date of Patent: Feb. 15, 2022

(54) LOW ACUITY DRESSING WITH INTEGRAL PUMP

(71) Applicant: KCI Licensing, Inc., San Antonio, TX (US)

(72) Inventors: Christopher Brian Locke, Bournemouth (GB); Richard Daniel John Coulthard, Verwood (GB); Timothy Mark Robinson, Shillingstone (GB)

(*) Notice: Subject to any disclaimer, the term of this patent is extended or adjusted under 35 U.S.C. 154(b) by 458 days.

(21) Appl. No.: 15/571,238

(22) PCT Filed: May 8, 2016

(86) PCT No.: PCT/US2016/031397
§ 371 (c)(1),
(2) Date: Nov. 1, 2017

(87) PCT Pub. No.: WO2016/182977
PCT Pub. Date: Nov. 17, 2016

(65) Prior Publication Data
US 2018/0272052 A1 Sep. 27, 2018

Related U.S. Application Data

(60) Provisional application No. 62/159,110, filed on May 8, 2015.

(51) Int. Cl.
*A61M 1/00* (2006.01)
*A61F 13/02* (2006.01)
*A61F 13/00* (2006.01)

(52) U.S. Cl.
CPC ......... *A61M 1/90* (2021.05); *A61F 13/00068* (2013.01); *A61F 13/0203* (2013.01);
(Continued)

(58) Field of Classification Search
CPC .. A61M 1/0088; A61M 1/0035; A61M 1/009; A61M 1/0052; A61M 1/0003;
(Continued)

(56) References Cited

U.S. PATENT DOCUMENTS 1,355,846 A 10/1920 Rannells
1,944,834 A 1/1934 Bennett
(Continued)

FOREIGN PATENT DOCUMENTS

AU 550575 B2 3/1986
AU 745271 B2 3/2002
(Continued)

OTHER PUBLICATIONS

Office Action for related U.S. Appl. No. 15/314,426, dated Aug. 29, 2019.
(Continued)

*Primary Examiner* — Andrew J Mensh

(57) ABSTRACT

Systems, assemblies, and methods for providing negative-pressure therapy to a tissue site are described. The system can include an absorbent and a sealing layer configured to cover the absorbent. The system can also include a blister fluidly coupled to the absorbent. The blister may have a collapsed position and an expanded position. A first check valve may be fluidly coupled to the absorbent and the blister and configured to prevent fluid flow from the blister into the absorbent if the blister is moved from the expanded position to the collapsed position. A second check valve may be fluidly coupled to the blister and the ambient environment and configured to prevent fluid flow from the ambient environment into the blister if the blister is moved from the collapsed position to the expanded position.

17 Claims, 9 Drawing Sheets

(52) U.S. Cl.
CPC ...... *A61F 13/0206* (2013.01); *A61F 13/0216* (2013.01); *A61M 1/743* (2021.05); *A61M 1/784* (2021.05); *A61M 1/962* (2021.05); *A61F 2013/0028* (2013.01); *A61F 2013/00119* (2013.01); *A61M 1/0003* (2013.01); *A61M 2205/0216* (2013.01); *A61M 2205/7536* (2013.01); *A61M 2205/7545* (2013.01); *A61M 2207/00* (2013.01)

(58) Field of Classification Search
CPC ...... A61M 2207/00; A61M 2205/7545; A61M 2205/7536; A61M 2205/0216; A61F 13/00068; A61F 13/0203; A61F 13/0216; A61F 13/0206; A61F 2013/0028; A61F 2013/00119
USPC ...................................................... 604/319
See application file for complete search history.

(56) References Cited

U.S. PATENT DOCUMENTS

| | | |
|---|---|---|
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,174,664 A | 11/1979 | Arnott et al. |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,323,069 A | 4/1982 | Ahr et al. |
| 4,333,468 A | 6/1982 | Geist |
| 4,343,848 A | 8/1982 | Leonard, Jr. |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,617,021 A | 10/1986 | Leuprecht |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,705,543 A | 11/1987 | Kertzman |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,773,408 A | 9/1988 | Cilento et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,842,594 A | 6/1989 | Ness |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,042,500 A | 8/1991 | Norlien et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,127,601 A | 7/1992 | Schroeder |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,244,457 A | 9/1993 | Karami et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,271,987 A | 12/1993 | Iskra |
| 5,278,100 A | 1/1994 | Doan et al. |
| 5,279,550 A | 1/1994 | Habib et al. |
| 5,298,015 A | 3/1994 | Komatsuzaki et al. |

(56) References Cited

U.S. PATENT DOCUMENTS

| | | | |
|---|---|---|---|
| 5,342,329 A | 8/1994 | Croquevielle | |
| 5,342,376 A | 8/1994 | Ruff | |
| 5,344,415 A | 9/1994 | DeBusk et al. | |
| 5,356,386 A | 10/1994 | Goldberg et al. | |
| 5,358,494 A | 10/1994 | Svedman | |
| 5,384,174 A | 1/1995 | Ward et al. | |
| 5,387,207 A | 2/1995 | Dyer et al. | |
| 5,419,769 A | 5/1995 | Devlin et al. | |
| 5,423,778 A | 6/1995 | Eriksson et al. | |
| 5,429,590 A | 7/1995 | Saito et al. | |
| 5,437,622 A | 8/1995 | Carion | |
| 5,437,651 A | 8/1995 | Todd et al. | |
| 5,445,604 A | 8/1995 | Lang | |
| 5,447,492 A * | 9/1995 | Cartmell | A61F 13/0203 602/41 |
| 5,458,938 A | 10/1995 | Nygard et al. | |
| 5,501,212 A | 3/1996 | Psaros | |
| 5,522,808 A | 6/1996 | Skalla | |
| 5,527,293 A | 6/1996 | Zamierowski | |
| 5,549,584 A * | 8/1996 | Gross | A61M 1/0088 604/313 |
| 5,549,585 A | 8/1996 | Maher et al. | |
| 5,556,375 A | 9/1996 | Ewall | |
| 5,585,178 A | 12/1996 | Calhoun et al. | |
| 5,599,292 A | 2/1997 | Yoon | |
| 5,607,388 A | 3/1997 | Ewall | |
| 5,611,373 A | 3/1997 | Ashcraft | |
| 5,634,893 A | 6/1997 | Rishton | |
| 5,636,643 A | 6/1997 | Argenta et al. | |
| 5,641,506 A | 6/1997 | Talke et al. | |
| 5,645,081 A | 7/1997 | Argenta et al. | |
| 5,653,224 A | 8/1997 | Johnson | |
| 5,678,564 A | 10/1997 | Lawrence et al. | |
| 5,710,233 A | 1/1998 | Meckel et al. | |
| 5,714,225 A | 2/1998 | Hansen et al. | |
| 5,736,470 A | 4/1998 | Schneberger et al. | |
| 5,759,570 A | 6/1998 | Arnold | |
| 5,776,119 A | 7/1998 | Bilbo et al. | |
| 5,807,295 A | 9/1998 | Hutcheon et al. | |
| 5,830,201 A | 11/1998 | George et al. | |
| 5,878,971 A | 3/1999 | Minnema | |
| 5,902,439 A | 5/1999 | Pike et al. | |
| 5,919,476 A | 7/1999 | Fischer et al. | |
| 5,941,863 A | 8/1999 | Guidotti et al. | |
| 5,964,252 A | 10/1999 | Simmons et al. | |
| 5,981,822 A | 11/1999 | Addison | |
| 5,998,561 A | 12/1999 | Jada | |
| 6,071,267 A | 6/2000 | Zamierowski | |
| 6,083,616 A | 7/2000 | Dressier | |
| 6,086,995 A | 7/2000 | Smith | |
| 6,135,116 A | 10/2000 | Vogel et al. | |
| 6,174,306 B1 | 1/2001 | Fleischmann | |
| 6,191,335 B1 | 2/2001 | Robinson | |
| 6,201,164 B1 | 3/2001 | Wulff et al. | |
| 6,228,485 B1 | 5/2001 | Leiter | |
| 6,238,762 B1 | 5/2001 | Friedland et al. | |
| 6,241,747 B1 | 6/2001 | Ruff | |
| 6,262,329 B1 | 7/2001 | Brunsveld et al. | |
| 6,287,316 B1 | 9/2001 | Agarwal et al. | |
| 6,345,623 B1 | 2/2002 | Heaton et al. | |
| 6,457,200 B1 | 10/2002 | Tanaka et al. | |
| 6,458,109 B1 | 10/2002 | Henley et al. | |
| 6,488,643 B1 * | 12/2002 | Tumey | A61F 5/0111 601/150 |
| 6,493,568 B1 | 12/2002 | Bell et al. | |
| 6,495,229 B1 | 12/2002 | Carte et al. | |
| 6,503,855 B1 | 1/2003 | Menzies et al. | |
| 6,529,532 B2 | 3/2003 | Kusnezow | |
| 6,548,727 B1 | 4/2003 | Swenson | |
| 6,553,998 B2 | 4/2003 | Heaton et al. | |
| 6,566,575 B1 | 5/2003 | Stickels et al. | |
| 6,566,577 B1 | 5/2003 | Addison et al. | |
| 6,626,891 B2 | 9/2003 | Ohmstede | |
| 6,627,215 B1 | 9/2003 | Dale et al. | |
| 6,648,862 B2 | 11/2003 | Watson | |
| 6,680,113 B1 | 1/2004 | Lucast et al. | |
| 6,685,681 B2 | 2/2004 | Lockwood et al. | |
| 6,693,180 B2 | 2/2004 | Lee et al. | |
| 6,695,823 B1 | 2/2004 | Lina et al. | |
| 6,752,794 B2 | 6/2004 | Lockwood et al. | |
| 6,787,682 B2 | 9/2004 | Gilman | |
| 6,814,079 B2 | 11/2004 | Heaton et al. | |
| 6,855,135 B2 | 2/2005 | Lockwood et al. | |
| 6,856,821 B2 | 2/2005 | Johnson | |
| 6,979,324 B2 | 12/2005 | Bybordi et al. | |
| 7,070,584 B2 | 7/2006 | Johnson et al. | |
| 7,154,017 B2 | 12/2006 | Sigurjonsson et al. | |
| 7,402,721 B2 | 7/2008 | Sigurjonsson et al. | |
| 7,569,742 B2 | 8/2009 | Haggstrom et al. | |
| 7,645,269 B2 * | 1/2010 | Zamierowski | A61M 1/0025 604/305 |
| 7,846,141 B2 | 12/2010 | Weston | |
| 7,880,050 B2 * | 2/2011 | Robinson | A61F 13/0203 602/44 |
| 7,942,866 B2 * | 5/2011 | Radi | A61M 1/0011 604/317 |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,298,197 B2 | 10/2012 | Eriksson et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,632,523 B2 | 1/2014 | Eriksson et al. | |
| 8,679,081 B2 | 3/2014 | Heagle et al. | |
| 8,764,732 B2 | 7/2014 | Hartwell | |
| 8,834,451 B2 | 9/2014 | Blott et al. | |
| 8,920,830 B2 | 12/2014 | Mathies | |
| 8,926,592 B2 | 1/2015 | Blott et al. | |
| 9,017,302 B2 | 4/2015 | Vitaris et al. | |
| 9,192,444 B2 | 11/2015 | Locke et al. | |
| 9,198,801 B2 | 12/2015 | Weston | |
| 9,211,365 B2 | 12/2015 | Weston | |
| 9,289,542 B2 | 3/2016 | Blott et al. | |
| 9,877,873 B2 | 1/2018 | Coulthard et al. | |
| 9,956,120 B2 | 5/2018 | Locke | |
| 2001/0030304 A1 | 10/2001 | Kohda et al. | |
| 2001/0051178 A1 | 12/2001 | Blatchford et al. | |
| 2002/0009568 A1 | 1/2002 | Bries et al. | |
| 2002/0016346 A1 | 2/2002 | Brandt et al. | |
| 2002/0065494 A1 | 5/2002 | Lockwood et al. | |
| 2002/0077661 A1 | 6/2002 | Saadat | |
| 2002/0090496 A1 | 7/2002 | Kim et al. | |
| 2002/0115951 A1 | 8/2002 | Norstrem et al. | |
| 2002/0119292 A1 | 8/2002 | Venkatasanthanam et al. | |
| 2002/0120185 A1 * | 8/2002 | Johnson | A61B 5/14542 600/364 |
| 2002/0130064 A1 | 9/2002 | Adams et al. | |
| 2002/0143286 A1 | 10/2002 | Tumey | |
| 2002/0150270 A1 | 10/2002 | Werner | |
| 2002/0150720 A1 | 10/2002 | Howard et al. | |
| 2002/0161346 A1 | 10/2002 | Lockwood et al. | |
| 2002/0164346 A1 | 11/2002 | Nicolette | |
| 2002/0183702 A1 | 12/2002 | Henley et al. | |
| 2002/0198504 A1 | 12/2002 | Risk et al. | |
| 2003/0014022 A1 | 1/2003 | Lockwood et al. | |
| 2003/0070680 A1 | 4/2003 | Smith et al. | |
| 2003/0109855 A1 | 6/2003 | Solem et al. | |
| 2003/0158577 A1 | 8/2003 | Ginn et al. | |
| 2003/0208175 A1 | 11/2003 | Gross et al. | |
| 2003/0212357 A1 | 11/2003 | Pace | |
| 2003/0225347 A1 | 12/2003 | Argenta et al. | |
| 2003/0225355 A1 | 12/2003 | Butler | |
| 2004/0002676 A1 | 1/2004 | Siegwart et al. | |
| 2004/0030304 A1 | 2/2004 | Hunt et al. | |
| 2004/0064132 A1 | 4/2004 | Boehringer et al. | |
| 2004/0077984 A1 | 4/2004 | Worthley | |
| 2004/0082925 A1 | 4/2004 | Patel | |
| 2004/0099268 A1 | 5/2004 | Smith et al. | |
| 2004/0118401 A1 | 6/2004 | Smith et al. | |

(56) References Cited

U.S. PATENT DOCUMENTS

| | | |
|---|---|---|
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radi et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1* | 11/2005 | Weston ............... A61M 1/0031 604/313 |
| 2005/0261643 A1 | 11/2005 | Bybordi et al. |
| 2005/0277860 A1 | 12/2005 | Jensen |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1* | 4/2007 | Haggstrom ......... A61M 1/0031 602/53 |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1* | 11/2007 | Joshi .................. A61M 1/0015 604/313 |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1* | 8/2008 | Robinson .......... A61F 13/00029 602/44 |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2008/0306456 A1* | 12/2008 | Riesinger ............ A61F 13/0203 604/316 |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0063467 A1 | 3/2010 | Addison et al. |
| 2010/0069863 A1 | 3/2010 | Olson |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0312159 A1 | 12/2010 | Aali et al. |
| 2010/0318072 A1 | 12/2010 | Johnston et al. |
| 2010/0324516 A1 | 12/2010 | Braga et al. |
| 2011/0046585 A1* | 2/2011 | Weston ............... A61F 15/008 604/320 |
| 2011/0054423 A1 | 3/2011 | Blott et al. |
| 2011/0118683 A1 | 5/2011 | Weston |
| 2011/0137271 A1* | 6/2011 | Andresen ............ A61F 5/443 604/319 |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |
| 2011/0237969 A1 | 9/2011 | Eckerbom et al. |
| 2011/0244010 A1 | 10/2011 | Doshi |
| 2011/0257612 A1 | 10/2011 | Locke et al. |
| 2011/0257617 A1 | 10/2011 | Franklin |
| 2011/0281084 A1 | 11/2011 | Ashwell |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123359 A1 | 5/2012 | Reed |
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Mitchell et al. |
| 2013/0172843 A1 | 7/2013 | Kurata |
| 2013/0189339 A1 | 7/2013 | Vachon |
| 2013/0261585 A1 | 10/2013 | Lee |
| 2013/0304007 A1 | 11/2013 | Toth |
| 2013/0330486 A1 | 12/2013 | Shields |
| 2014/0012213 A1* | 1/2014 | Locke .................. A61F 13/025 604/319 |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |

(56) References Cited

U.S. PATENT DOCUMENTS

| | | | |
|---|---|---|---|
| 2014/0141197 A1 | 5/2014 | Hill et al. | |
| 2014/0155849 A1* | 6/2014 | Heaton | A61M 39/24 604/321 |
| 2014/0163491 A1 | 6/2014 | Schuessler et al. | |
| 2014/0171851 A1 | 6/2014 | Addison | |
| 2014/0178564 A1 | 6/2014 | Patel | |
| 2014/0200533 A1* | 7/2014 | Whyte | A61M 1/0088 604/319 |
| 2014/0276490 A1 | 9/2014 | Locke et al. | |
| 2014/0309574 A1 | 10/2014 | Cotton | |
| 2014/0336557 A1 | 11/2014 | Durdag et al. | |
| 2014/0350494 A1 | 11/2014 | Hartwell et al. | |
| 2014/0352073 A1 | 12/2014 | Goenka | |
| 2015/0030848 A1 | 1/2015 | Goubard | |
| 2015/0045752 A1 | 2/2015 | Grillitsch et al. | |
| 2015/0057625 A1 | 2/2015 | Coulthard | |
| 2015/0080788 A1 | 3/2015 | Blott et al. | |
| 2015/0080815 A1 | 3/2015 | Chakravarthy et al. | |
| 2015/0119830 A1 | 4/2015 | Luckemeyer et al. | |
| 2015/0119833 A1 | 4/2015 | Coulthard et al. | |
| 2015/0119834 A1 | 4/2015 | Locke et al. | |
| 2015/0141941 A1 | 5/2015 | Allen et al. | |
| 2015/0190286 A1 | 7/2015 | Allen et al. | |
| 2015/0290041 A1 | 10/2015 | Richard | |
| 2016/0000610 A1 | 1/2016 | Riesinger | |
| 2016/0067107 A1 | 3/2016 | Cotton | |
| 2016/0144084 A1 | 5/2016 | Collinson et al. | |

FOREIGN PATENT DOCUMENTS

| | | | |
|---|---|---|---|
| AU | 755496 B2 | 12/2002 | |
| AU | 2009200608 A1 | 10/2009 | |
| CA | 2005436 A1 | 6/1990 | |
| CN | 87101823 A | 8/1988 | |
| DE | 26 40 413 A1 | 3/1978 | |
| DE | 43 06 478 A1 | 9/1994 | |
| DE | 29 504 378 U1 | 9/1995 | |
| DE | 202004018245 U1 | 7/2005 | |
| DE | 202014100383 U1 | 2/2015 | |
| EP | 0097517 A1 | 1/1984 | |
| EP | 0100148 A1 | 2/1984 | |
| EP | 0117632 A2 | 9/1984 | |
| EP | 0161865 A2 | 11/1985 | |
| EP | 0251810 A2 | 1/1988 | |
| EP | 0275353 A2 | 7/1988 | |
| EP | 0358302 A2 | 3/1990 | |
| EP | 0538917 A1 | 4/1993 | |
| EP | 0630629 A1 | 12/1994 | |
| EP | 0659390 A2 | 6/1995 | |
| EP | 0633758 B1 | 10/1996 | |
| EP | 1002846 A1 | 5/2000 | |
| EP | 1018967 A1 | 7/2000 | |
| EP | 2578193 A1 | 4/2013 | |
| GB | 692578 A | 6/1953 | |
| GB | 1386800 A | 3/1975 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2377939 A | 1/2003 | |
| GB | 2392836 A | 3/2004 | |
| GB | 2393655 A | 4/2004 | |
| GB | 2425487 A | 11/2006 | |
| GB | 2452720 A | 3/2009 | |
| GB | 2496310 A | 5/2013 | |
| JP | 1961003393 | 2/1961 | |
| JP | S62139523 U | 9/1987 | |
| JP | S62-275456 A | 11/1987 | |
| JP | 2005205120 A | 8/2005 | |
| JP | 2007254515 A | 10/2007 | |
| JP | 2008080137 A | 4/2008 | |
| JP | 4129536 B2 | 8/2008 | |
| JP | 2012050274 A | 3/2012 | |
| SG | 71559 | 4/2002 | |
| WO | 80/02182 A1 | 10/1980 | |
| WO | 87/04626 A1 | 8/1987 | |
| WO | 8707164 A1 | 12/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 9622753 A1 | 8/1996 | |
| WO | 97/18007 A1 | 5/1997 | |
| WO | 99/13793 A1 | 3/1999 | |
| WO | 99/65542 A1 | 12/1999 | |
| WO | 01/36188 A1 | 5/2001 | |
| WO | 01/60296 A1 | 8/2001 | |
| WO | 0168021 A1 | 9/2001 | |
| WO | 0185248 A1 | 11/2001 | |
| WO | 3190465 A2 | 11/2001 | |
| WO | 0243743 A1 | 6/2002 | |
| WO | 02062403 A1 | 8/2002 | |
| WO | 03-018098 A2 | 3/2003 | |
| WO | 03045294 A1 | 6/2003 | |
| WO | 03045492 A1 | 6/2003 | |
| WO | 03053484 A1 | 7/2003 | |
| WO | 2004024197 A1 | 3/2004 | |
| WO | 2004037334 A1 | 5/2004 | |
| WO | 2004112852 A1 | 12/2004 | |
| WO | 2005002483 A2 | 1/2005 | |
| WO | 2005062896 A2 | 7/2005 | |
| WO | 2005105176 A1 | 11/2005 | |
| WO | 2005123170 A1 | 12/2005 | |
| WO | 2007022097 A2 | 2/2007 | |
| WO | 2007030601 A2 | 3/2007 | |
| WO | 2007070269 A1 | 6/2007 | |
| WO | 2007085396 A1 | 8/2007 | |
| WO | 2007087811 A1 | 8/2007 | |
| WO | 2007113597 A2 | 10/2007 | |
| WO | 2007133618 A2 | 11/2007 | |
| WO | 2008026117 A1 | 3/2008 | |
| WO | 2008/041926 A1 | 4/2008 | |
| WO | 2008048527 A2 | 4/2008 | |
| WO | 2008054312 A1 | 5/2008 | |
| WO | 2008/082444 A2 | 7/2008 | |
| WO | 2008/100440 A1 | 8/2008 | |
| WO | 2008104609 A1 | 9/2008 | |
| WO | 2008/131895 A1 | 11/2008 | |
| WO | 2009/002260 A1 | 12/2008 | |
| WO | 2008149107 A1 | 12/2008 | |
| WO | 2009066105 A1 | 5/2009 | |
| WO | 2009066106 A1 | 5/2009 | |
| WO | 2009081134 A1 | 7/2009 | |
| WO | 2009089016 A1 | 7/2009 | |
| WO | 2009/124100 A1 | 10/2009 | |
| WO | 2009126103 A1 | 10/2009 | |
| WO | 2010011148 A1 | 1/2010 | |
| WO | 2010016791 A1 | 2/2010 | |
| WO | 2010032728 A1 | 3/2010 | |
| WO | 2010/056977 A2 | 5/2010 | |
| WO | 2010129299 A2 | 11/2010 | |
| WO | 2011008497 A2 | 1/2011 | |
| WO | 2011/049562 A1 | 4/2011 | |
| WO | 2011043786 A1 | 4/2011 | |
| WO | 2011115908 A1 | 9/2011 | |
| WO | 2011121127 A1 | 10/2011 | |
| WO | 2011130570 A1 | 10/2011 | |
| WO | 2011162862 A1 | 12/2011 | |
| WO | WO-2011162862 A1 * | 12/2011 | ......... A61F 13/0216 |
| WO | 2012/112204 A1 | 8/2012 | |
| WO | 2012104584 A1 | 8/2012 | |
| WO | 2012140378 A1 | 10/2012 | |
| WO | 2012143665 A1 | 10/2012 | |
| WO | 2013009239 A1 | 1/2013 | |
| WO | 2013066426 A2 | 5/2013 | |
| WO | 2013090810 A1 | 6/2013 | |
| WO | 2014022400 A1 | 2/2014 | |
| WO | 2014039557 A1 | 3/2014 | |
| WO | 2014078518 A1 | 5/2014 | |
| WO | 2014/113253 A1 | 7/2014 | |
| WO | 2014140608 A1 | 9/2014 | |

(56) References Cited

FOREIGN PATENT DOCUMENTS

| WO | 2014143488 A1 | 9/2014 |
|---|---|---|
| WO | 2015/065615 A1 | 5/2015 |
| WO | 2015130471 A1 | 9/2015 |
| WO | 2017048866 A1 | 3/2017 |

OTHER PUBLICATIONS

Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.
Office Action for related U.S. Appl. No. 15/410,991, dated May 2, 2019.
International Search Report and Written Opinion dated Oct. 19, 2010; PCT International Application No. PCT/US2009/036217.
NPD 1000 Negative Pressure Would Therapy System, Kalypto Medical, pp. 1-4, dated Sep. 2008.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
International Search Report and Written opinion for PCT Application PCT/US2009/036222, dated Dec. 15, 2009.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
Extended European Search Report for corresponding Application No. 15194949.2, dated Mar. 11, 2016.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion for PCT International Application No. PCT/US2011/028344, dated Jan. 6, 2011.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
European Search Report for corresponding EP Application 171572787 dated Jun. 6, 2017.
Office Action for related U.S. Appl. No. 15/307,472, dated Oct. 18, 2018.
European Search Report for corresponding application 17167872.5, dated Aug. 14, 2017.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Japanese office action for related application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related application PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
Extended European Search Report for related application 17177013.4, dated Mar. 19, 2018.
Extended European Search Report for related application 16793298.7, dated Mar. 27, 2018.
Office Action for related U.S. Appl. No. 14/965,675, dated Aug. 9, 2018.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.

(56) References Cited

OTHER PUBLICATIONS

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

"D.E. Tribble, An Improved Sump Drain-Irrigation Device of Simple Construction," Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

ISR for corresponding PCT/US2016/031397 dated Aug. 8, 2016.

Office Action for related U.S. Appl. No. 15/600,451, dated Nov. 27, 2019.

Australian Office Action for related application 2018278874, dated Feb. 12, 2020.

Office Action for related U.S. Appl. No. 14/630,290, dated Apr. 30, 2020.

Office Action for related U.S. Appl. No. 15/793,044, dated May 13, 2020.

EP Informal Search Report for related application 19186600.3.

Office Action for related U.S. Appl. No. 15/884,198, dated May 19, 2020.

Office Action for related U.S. Appl. No. 16/007,060, dated Aug. 18, 2020.

Office Action for related U.S. Appl. No. 15/937,485, dated Aug. 4, 2020.

Office Action for related U.S. Appl. No. 15/793,044, dated Sep. 24, 2020.

Extended European Search Report for related application 20185730.7, dated Oct. 9, 2020.

Advisory Action for related U.S. Appl. No. 15/793,044, dated Dec. 9, 2020.

Japanese Office Action for related application 2019-235427, dated Jan. 5, 2021.

Office Action for related U.S. Appl. No. 16/151,005, dated Apr. 13, 2021.

Office Action for related U.S. Appl. No. 16/287,862, dated Nov. 2, 2021.

\* cited by examiner

LOW ACUITY DRESSING WITH INTEGRAL PUMP

RELATED APPLICATION

This application claims the benefit, under 35 USC 119(e), of the filing of U.S. Provisional Patent Application No. 62/159,110, entitled "Low-Acuity Dressing with Integral Pump," filed May 8, 2015, which is incorporated herein by reference for all purposes.

TECHNICAL FIELD

The invention set forth in the appended claims relates generally to tissue treatment systems and more particularly, but without limitation, to a dressing having an integral pump for low-acuity tissue sites.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for providing negative-pressure therapy are set forth in the appended claims. Illustrative embodiments are also provided to enable a person skilled in the art to make and use the claimed subject matter. For example, a system for providing negative-pressure therapy to a tissue site is described. The system can include an absorbent and a sealing layer configured to cover the absorbent. The system can also include a blister fluidly coupled to the absorbent. The blister may have a collapsed position and an expanded position. A first check valve may be fluidly coupled to the absorbent and the blister and configured to prevent fluid flow from the blister into the absorbent if the blister is moved from the expanded position to the collapsed position. A second check valve may be fluidly coupled to the blister and the ambient environment and configured to prevent fluid flow from the ambient environment into the blister if the blister is moved from the collapsed position to the expanded position.

Alternatively, other example embodiments describe a dressing assembly for providing negative-pressure therapy to a tissue site. The dressing assembly can include a pouch and a cover configured to cover the pouch. A negative-pressure source may be fluidly coupled to the pouch. The negative-pressure source may have a first position and a second position. A first check valve may be fluidly coupled to the pouch and the negative-pressure source and operable to prevent fluid flow from the negative-pressure source into the pouch if the negative-pressure source is moved from the second position to the first position. A second check valve may be fluidly coupled to the negative-pressure source and the ambient environment and configured to prevent fluid flow from the ambient environment into the negative-pressure source if the negative-pressure source is moved from the first position to the second position.

A method for providing negative-pressure therapy to a tissue site is also described herein. A dressing assembly may be positioned adjacent to the tissue site. The dressing assembly may have an absorbent; a sealing layer configured to cover the absorbent; and a blister fluidly coupled to the absorbent. The blister may have a collapsed position and an expanded position. A first check valve may be fluidly coupled to the absorbent and the blister and configured to prevent fluid flow from the blister into the absorbent if the blister is moved from the expanded position to the collapsed position. A second check valve may be fluidly coupled to the blister and the ambient environment and configured to prevent fluid flow from the ambient environment into the blister if the blister is moved from the collapsed position to the expanded position. The blister may be compressed from the expanded position to the collapsed position to evacuate the blister. The blister may expand from the collapsed position to the expanded position to draw fluid from the absorbent.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
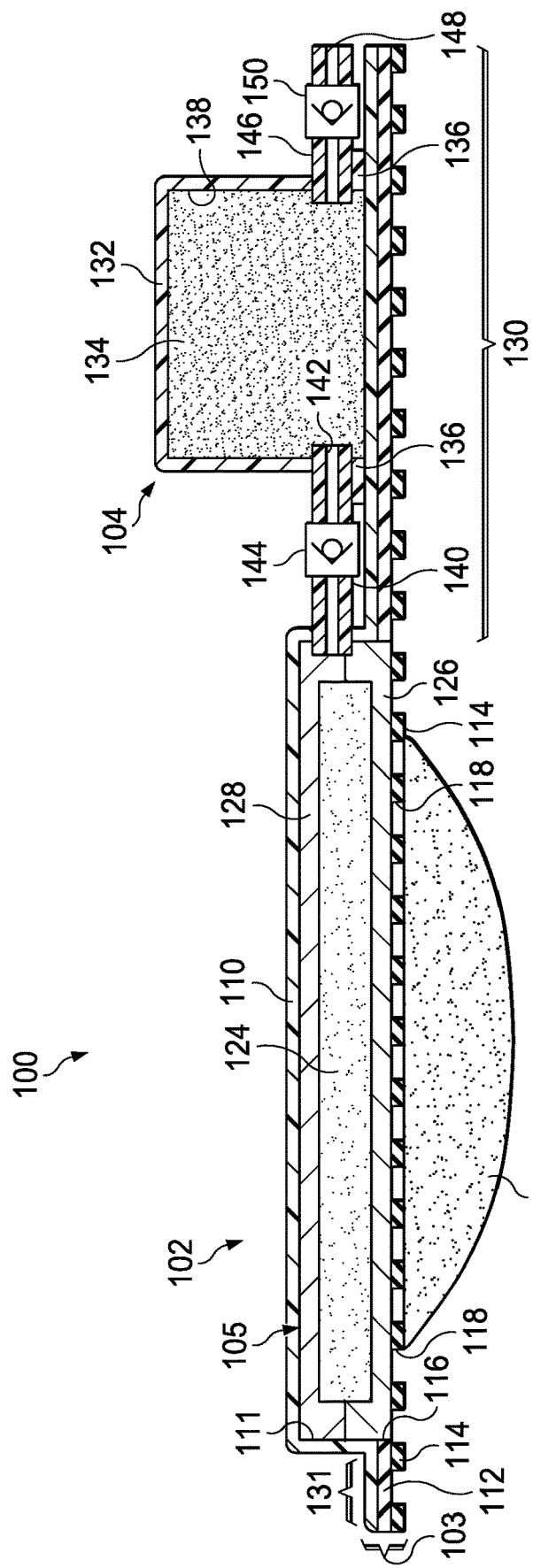
FIG. 1 is a sectional view of an example embodiment of a negative-pressure therapy system that can provide negative-pressure therapy in accordance with this specification.

FIG. 1 is a sectional view of an example embodiment of a negative-pressure therapy system 100 that can provide negative-pressure therapy in accordance with this specification. The negative-pressure therapy system 100 may include a dressing assembly and a tissue interface. For example, a tissue interface 108 may be placed in a tissue site and a dressing assembly 102 may be placed over the tissue site and the tissue interface 108. The dressing assembly 102 may include a cover 103 and a pouch 105 which may be fluidly coupled to a negative-pressure source 104.

In general, components of the negative-pressure therapy system 100 may be coupled directly or indirectly. For example, the negative-pressure source 104 may be directly coupled to the pouch 105 and indirectly coupled to the tissue site through the pouch 105. Components may be fluidly coupled to each other to provide a path for transferring fluids (i.e., liquid and/or gas) between the components.

In some embodiments, components may be fluidly coupled through a tube, such as a tube 140 or a tube 146. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 108 may be placed within, over, on, or otherwise proximate to a tissue site. The cover 103 may be placed over the tissue interface 108 and sealed to tissue near the tissue site. For example, the cover 103 may be sealed to undamaged epidermis peripheral to a tissue site. Thus, the dressing assembly 102 can provide a sealed therapeutic environment proximate to a tissue site, substantially isolated from the external environment, and the negative-pressure source 104 can reduce the pressure in the sealed therapeutic environment. The sealed therapeutic environment may be formed in the space occupied by the tissue interface 108 and the pouch 105. If the tissue interface 108 is not used, the sealed therapeutic environment may be formed in the space occupied by the pouch 105 and the tissue site. Negative pressure applied across the tissue site in the sealed therapeutic environment can induce macrostrain and microstrain in the tissue site, as well as remove exudates and other fluids from the tissue site, which can be collected in the pouch 105 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing assembly 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites.

In some embodiments, the tissue interface 108 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels that are interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 108 may be made from a hydrophilic material, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In some embodiments, the tissue interface 108 may be combined with hemostat material and anti-microbial materials to treat tissue sites that may have a significant depth.

In some embodiments, the cover 103 may be a sealing layer and provide a bacterial barrier and protection from physical trauma. The cover 103 may also be constructed from a material that can reduce evaporative losses and provide a fluid seal between two components or two environments, such as between a therapeutic environment and a local external environment. The cover 103 may be, for example, an elastomeric film or membrane that can provide a seal adequate to maintain a negative pressure at a tissue site for a given negative-pressure source. In some example embodiments, the cover 103 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 103 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 103 may be coated with an acrylic adhesive having a coating weight between 25-65 g.s.m. Thicker adhesives, or combinations of adhesives, may be applied in some embodiments, to improve the seal and reduce leaks. Other example embodiments of an attachment device may include a double-sided tape, paste, hydrocolloid, hydrogel, silicone gel, or organogel.

Typically, patients having low-acuity tissue sites may be mobile and may not require confinement to a care facility during the duration of the treatment of the tissue site. Consequently, a dedicated negative-pressure therapy system that requires a continuous supply of electrical current to provide negative-pressure therapy may not be preferable for use as a treatment device. Ambulatory patients may receive beneficial negative-pressure therapy by using the negative-pressure therapy system 100 described herein, which provides a peel-and-place dressing and negative-pressure source that allows the patient to easily see the status of the negative-pressure therapy and to reapply negative-pressure therapy without the intervention of a clinician.

As shown in FIG. 1, the negative-pressure therapy system 100 can include the tissue interface 108 and the dressing assembly 102 having the cover 103, the pouch 105, and the negative-pressure source 104. The cover 103, the pouch 105, and the negative-pressure source 104 may be coupled to each other and collectively placed over the tissue interface 108 and undamaged epidermis.

The pouch 105 may include an absorbent 124, a first outer layer, such as an upstream layer 126, and a second outer layer, such as a downstream layer 128. The upstream layer 126 and the downstream layer 128 may envelop or enclose the absorbent 124. The absorbent 124 may hold, stabilize, and/or solidify fluids collected from the tissue site. The absorbent 124 may be formed from materials referred to as "hydrogels," "super-absorbents," or "hydrocolloids." If disposed within the dressing assembly 102, the absorbent 124 may be formed into fibers or spheres to manifold negative pressure until the absorbent 124 becomes saturated. Spaces or voids between the fibers or spheres may allow a negative pressure that is supplied to the dressing assembly 102 to be transferred within and through the absorbent 124 to the tissue interface 108 and the tissue site. In some exemplary embodiments, the absorbent 124 may be Texsus FP2325 having a material density of about 800 grams per square meter (gsm). In other exemplary embodiments, the absorbent material may be BASF 402C, Technical Absorbents 2317 available from Technical Absorbents (www.techabsorbents.com), sodium polyacrylate super absorbers, cellulosics (carboxy methyl cellulose and salts such as sodium CMC), or alginates.

In some exemplary embodiments, the absorbent 124 may be formed of granular absorbent components that may be scatter coated onto a paper substrate. Scatter coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate may be passed through a calender machine to provide a smooth uniform surface to the absorbent material.

In some exemplary embodiments, the upstream layer 126 and the downstream layer 128 have perimeter dimensions that may be larger than the perimeter dimensions of the absorbent 124 so that, if the absorbent 124 is positioned between the upstream layer 126 and the downstream layer 128 and the center portions of the absorbent 124, the upstream layer 126, and the downstream layer 128 are aligned, the upstream layer 126 and the downstream layer 128 may extend beyond the perimeter of the absorbent 124. In some exemplary embodiments, the upstream layer 126 and the downstream layer 128 surround the absorbent 124. Peripheral portions of the upstream layer 126 and the downstream layer 128 may be coupled so that the upstream layer 126 and the downstream layer 128 enclose the absorbent 124. The upstream layer 126 and the downstream layer 128 may be coupled by high frequency welding, ultrasonic welding, heat welding, or impulse welding, for example. In other exemplary embodiments, the upstream layer 126 and the downstream layer 128 may be coupled by bonding or folding, for example.

The upstream layer 126 may be formed of non-woven material in some embodiments. For example, the upstream layer 126 may have a polyester fibrous porous structure. The upstream layer 126 may be porous, but preferably the upstream layer 126 is not perforated. The upstream layer 126 may have a material density between about 80 gsm and about 150 gsm. In other exemplary embodiments, the material density may be lower or greater depending on the particular application of the pouch 105. In some embodiments, the upstream layer 126 may be a plurality of layers of non-woven material. The upstream layer 126 may be formed of Libeltex TDL2, for example. In other embodiments, the upstream layer 126 may also be formed of Libeltex TL4.

The downstream layer 128 may also be formed of a non-woven material in some embodiments. For example, the downstream layer 128 may have a polyester fibrous porous structure. The downstream layer 128 may be porous, but the downstream layer 128 preferably is not perforated. The downstream layer 128 may have a material density between about 80 gsm and about 150 gsm. In other exemplary embodiments, the material density may be lower or greater depending on the particular application of the pouch 105. The material density of the downstream layer 128 may be greater or less than the material density of the upstream layer 126. In some embodiments, a thickness of the downstream layer 128 may be greater than a thickness of the upstream layer 126. In other embodiments, the thickness of the downstream layer 128 may be less than the thickness of the upstream layer 126. In some embodiments, the downstream layer 128 may be a plurality of layers of non-woven material. The downstream layer 128 may be formed of Libeltex TL4. In other exemplary embodiments, the downstream layer 128 may be formed of Libeltex TDL2.

The upstream layer 126 and the downstream layer 128 may be manifolding layers configured to facilitate fluid movement through the pouch 105. In some embodiments, the upstream layer 126 and the downstream layer 128 may each have a hydrophobic side and a hydrophilic side. The hydrophobic side may also be referred to as a wicking side, wicking surface, distribution surface, distribution side, or fluid distribution surface. The hydrophobic side may be a smooth distribution surface configured to move fluid along a grain of the upstream layer 126 and the downstream layer 128, distributing fluid throughout the upstream layer 126 and the downstream layer 128. The hydrophilic side may be configured to acquire bodily fluid from the hydrophobic side to aid in bodily fluid movement into the absorbent 124. The hydrophilic side may also be referred to as a fluid acquisition surface, fluid acquisition side, hydrophilic acquisition surface, or hydrophilic acquisition side. The hydrophilic side may be a fibrous surface and be configured to draw fluid into the upstream layer 126 and the downstream layer 128. In some embodiments, the hydrophilic side of the upstream layer 126 and the downstream layer 128 may be positioned adjacent to the absorbent 124. In other embodiments, the hydrophobic side of the upstream layer 126 and the downstream layer 128 may be positioned adjacent to the absorbent 124. In still other embodiments, the hydrophilic side of one of the upstream layer 126 or the downstream layer 128 may be positioned adjacent to the absorbent 124, and the hydrophobic side of the other of the upstream layer 126 or the downstream layer 128 may be positioned adjacent to the absorbent 124.

In some embodiments, the cover 103 may include or may be a hybrid drape having a barrier layer 110, a bonding adhesive layer 112, and a sealing adhesive layer 114. The barrier layer 110 may be formed from a range of medically approved films ranging in thickness from about 15 microns (μm) to about 50 microns (μm). The barrier layer 110 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the barrier layer 110 may be formed from a breathable cast matt polyurethane film sold by Expopack Advanced Coatings of Wrexham, United Kingdom, under the name INSPIRE 2301.

The barrier layer 110 may have a high moisture vapor transmission rate (MVTR). The MVTR of the barrier layer 110 allows vapor to egress and inhibits liquids from exiting. In some embodiments, the MVTR of the barrier layer 110 may be greater than or equal to 300 $g/m^2/24$ hours. In other embodiments, the MVTR of the barrier layer 110 may be greater than or equal to 1,000 $g/m^2/24$ hours. The illustrative INSPIRE 2301 film may have an MVTR (inverted cup technique) of 14,400 $g/m^2/24$ hours and may be approximately 30 microns thick. In other embodiments, a drape having a low MVTR or that allows no vapor transfer might be used. The barrier layer 110 can also function as a barrier to liquids and microorganisms.

In some embodiments, the barrier layer 110 may be adapted to form a bulge on a first side of the barrier layer and a cavity 111 on an opposite side of the barrier layer from the bulge. For example, the barrier layer 110 may be placed on a mold and stretched to plastically deform a portion of the barrier layer 110, forming the cavity 111. A periphery of the barrier layer 110 that is not stretched by the formation of the cavity 111 may form a flange surrounding the cavity 111. In some embodiments, the cavity 111 may be positioned so that a portion of the flange may be larger on a first side of the cavity 111 than on a second side of the cavity 111. The disparity in sizes of the flange may form a foundational flange 130 and a sealing flange 131. In some embodiments, the pouch 105 may be disposed in the cavity 111. The cavity 111 may also be a portion of the barrier layer 110 that is free of adhesive. For example, during manufacturing, a portion of the barrier layer 110 may be left without the bonding adhesive layer 112; the area of the barrier layer 110 without the bonding adhesive layer 112 may be equal to a surface area of the pouch 105 to be covered by the barrier layer 110.

The foundational flange 130 may extend away from the cavity 111. In some embodiments, the foundational flange 130 may have a length and a width sufficient to permit other objects to be coupled to the dressing assembly 102. For example, the foundational flange 130 may support the negative-pressure source 104, as illustrated in FIG. 1.

The bonding adhesive layer 112 may be coupled to the barrier layer 110 on a side of the barrier layer 110 having an opening of the cavity 111. In some embodiments, the bonding adhesive layer 112 may include an aperture 116. The aperture 116 may be coextensive with the opening of the cavity 111. For example, the bonding adhesive layer 112 may cover the barrier layer 110 at the foundational flange 130 and the sealing flange 131, leaving the portion of the barrier layer 110 forming the cavity 111 free of the bonding adhesive layer 112.

The bonding adhesive layer 112 may comprise an acrylic adhesive, rubber adhesive, high-tack silicone adhesive, polyurethane, or other substance. In an illustrative example, the bonding adhesive layer 112 comprises an acrylic adhesive with coating weight of 15 grams/m$^2$ (gsm) to 70 grams/m$^2$ (gsm). The bonding adhesive layer 112 may be a continuous layer of material or may be a layer with apertures (not shown). The apertures may be formed after application of the bonding adhesive layer 112 or may be formed by coating the bonding adhesive layer 112 in patterns on a carrier layer. In some embodiments, the bond strength of the bonding adhesive may have a peel adhesion or resistance to being peeled from a stainless steel material between about 6N/25 mm to about 10N/25 mm on stainless steel substrate at 23° C. at 50% relative humidity based on the American Society for Testing and Materials ("ASTM") standard ASTM D3330. The bonding adhesive layer 112 may be about 30 microns to about 60 microns in thickness.

The sealing adhesive layer 114 may be coupled to the bonding adhesive layer 112 and the pouch 105. For example, the sealing adhesive layer 114 may cover the sealing flange 131, the pouch 105, and the foundational flange 130. The sealing adhesive layer 114 may be formed with the plurality of apertures 118. The apertures 118 may be numerous shapes, for example, circles, squares, stars, ovals, polygons, slits, complex curves, rectilinear shapes, triangles, or other shapes. Each aperture 118 of the plurality of apertures 118 may have an effective diameter, which is the diameter of a circular area having the same surface area as the aperture 118. The average effective diameter of each aperture 118 may typically be in the range of about 6 mm to about 50 mm. The plurality of apertures 118 may have a uniform pattern or may be randomly distributed in the sealing adhesive layer 114. Generally, the apertures 118 may be disposed across a length and width of the sealing adhesive layer 114.

The sealing adhesive layer 114 may comprise a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 30 gsm-70 gsm acrylic), polyurethane, polyolefin, or hydrogenated styrenic copolymers. The sealing adhesive layer 114 may have a thickness in the range of about 100 microns (μm) to about 1,000 microns (μm). In some embodiments, the sealing adhesive layer 114 may have stiffness between about 5 Shore OO and about 80 Shore OO. The sealing adhesive layer 114 may be hydrophobic or hydrophilic. The sealing adhesive of the sealing adhesive layer 114 may be an adhesive having a low to medium tackiness, for example, a silicone polymer, polyurethane, or an additional acrylic adhesive. In some embodiments, the bond strength of the sealing adhesive may have a peel adhesion or resistance to being peeled from a stainless steel material between about 0.5N/25 mm to about 1.5N/25 mm on stainless steel substrate at 23° C. at 50% relative humidity based on ASTM D3330. The sealing adhesive may have a tackiness such that the sealing adhesive may achieve the bond strength above after a contact time of less than about 60 seconds. Tackiness may be considered a bond strength of an adhesive after a very low contact time between the adhesive and a substrate. In some embodiments, the sealing adhesive layer 114 may have a tackiness that may be about 30% to about 50% of the tackiness of the bonding adhesive of the bonding adhesive layer 112.

In the assembled state, the bonding adhesive layer 112 may be coupled to the barrier layer 110. The sealing adhesive layer 114 may be coupled to the bonding adhesive layer 112 at the sealing flange 131 and the foundational flange 130 and to the pouch 105 at the cavity 111. In some embodiments, a scrim layer may be disposed in the sealing adhesive layer 114. The scrim layer may provide additional mechanical support for the sealing adhesive layer 114. In some embodiments, the sealing adhesive layer 114 may be treated on a portion and a side of the sealing adhesive layer 114 adjacent to the pouch 105. The treated portion of the sealing adhesive layer 114 may reduce the tackiness of the sealing adhesive layer 114 so that the sealing adhesive layer 114 may not readily adhere to the pouch 105. The initial tackiness of the sealing adhesive layer 114 is preferably sufficient to initially couple the sealing adhesive layer 114 to the epidermis by forming sealing couplings. Once in the desired location, a force can be applied to the barrier layer 110 of the cover 103. For example, the user may rub the foundational flange 130 and the sealing flange 131. This action can cause at least a portion of the bonding adhesive layer 112 to be forced into the plurality of apertures 118 and into contact with the epidermis to form bonding couplings. The bonding couplings provide secure, releasable mechanical fixation to the epidermis.

The average effective diameter of the plurality of apertures 118 for the sealing adhesive layer 114 may be varied as one control of the tackiness or adhesion strength of the cover 103. In this regard, there is interplay between three main variables for each embodiment: the thickness of the sealing adhesive layer 114, the average effective diameter of the plurality of apertures 118, and the tackiness of the bonding adhesive layer 112. The more bonding adhesive of the bonding adhesive layer 112 that extends through the apertures 118, the stronger the bond of the bonding coupling. The thinner the sealing adhesive layer 114, the more bonding adhesive of the bonding adhesive layer 112 generally extends through the apertures 118 and the greater the bond of the bonding coupling. As an example of the interplay, if a very tacky bonding adhesive layer 112 is used and the thickness of the sealing adhesive layer 114 is small, the average effective diameter of the plurality of apertures 118 may be relatively smaller than if the bonding adhesive layer 112 is less tacky and the sealing adhesive layer 114 is thicker. In some embodiments, the thickness of the sealing adhesive layer 114 may be approximately 200 microns, the thickness of the bonding adhesive layer 112 may be approximately 30 microns with a tackiness of 2000 g/25 cm wide strip, and the average effective diameter of each aperture 118 may be approximately 6 mm.

As illustrated in FIG. 1, the negative-pressure source 104, which may also be referred to as a blister, may be coupled to the barrier layer 110 of the foundational flange 130. The negative-pressure source 104 may include a barrier layer and a biasing member, for example, a film layer 132 and a foam block 134. In some embodiments, the film layer 132 may form a source flange 136 and a source cavity 138. The source cavity 138 may be a portion of the film layer 132 that is plastically deformed, such as by vacuum forming, thermoforming, micro-thermoforming, injection molding, or blow molding, for example. In some embodiments, the source cavity 138 may form walls of the negative-pressure source 104 that may be resilient or flexible. The source flange 136 may be a portion of the film layer 132 adjacent to and surrounding an opening of the source cavity 138. In some embodiments, the foam block 134 may be disposed in the source cavity 138. The source flange 136 may be coupled to the barrier layer 110 of the foundational flange 130 to seal the foam block 134 in the source cavity 138. In some embodiments, the source flange 136 may be coupled to the barrier layer 110 by high frequency welding, ultrasonic welding, heat welding, or impulse welding, for example. In other exemplary embodiments, the source flange 136 may be coupled to the barrier layer 110 by bonding or folding, for example. In some embodiments, if the source flange 136 is coupled to the barrier layer 110 of the foundational flange 130, the source cavity 138 may be fluidly isolated from the ambient environment and the pouch 105.

The film layer 132 may be constructed from a material that can provide a fluid seal between two components or two environments, such as between the source cavity 138 and a local external environment, while allowing for repeated elastic deformation of the film layer 132. The film layer 132 may be, for example, an elastomeric film or membrane that can provide a seal between the source cavity 138 and the ambient environment. In some example embodiments, the film layer 132 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In an exemplary embodiment, the film layer 132 may be a polyurethane having a thickness between about 50 microns and about 250 microns and preferably about 100 microns.

The foam block 134 may be a foam having a plurality of interconnected flow channels. For example, cellular foam, open-cell foam, reticulated foam, porous tissue collections, and other porous material that generally include pores, edges, and/or walls adapted to form interconnected fluid pathways. Liquids, gels, and other foams may also include or be cured to include apertures and flow channels. In some illustrative embodiments, the foam block 134 may be a porous foam material having interconnected cells or pores adapted to uniformly (or quasi-uniformly) distribute fluid throughout the foam block 134. The foam material may be either hydrophobic or hydrophilic. In one non-limiting example, the foam block 134 may be an open-cell, reticulated polyurethane foam such as GranuFoam® dressing available from Kinetic Concepts, Inc. of San Antonio, Tex. Another exemplary embodiment of the foam block 134 may be Z48AA foam from FXI®. In some embodiments, the foam block 134 may include an indicator, such as a color change dye. The indicator may change colors if contacted by a liquid. Consequently, if the foam block 134 changes colors, a user may know that the dressing assembly 102 is saturated.

Foam materials may have an elastic modulus, which may also be referred to as a foam modulus. Generally, the elastic modulus of a material may measure the resistance of the material to elastic deformation under a load. The elastic modulus of a material may be defined as the slope of a stress-strain curve in the elastic deformation region of the curve. The elastic deformation region of a stress-strain curve represents that portion of the curve where a deformation of a material due to an applied load is elastic, that is, not permanent. If the load is removed, the material may return to its pre-loaded state. Stiffer materials may have a higher elastic modulus, and more compliant materials may have a lower elastic modulus. Generally, references to the elastic modulus of a material refers to a material under tension.

For some materials under compression, the elastic modulus can be compared between materials by comparing the compression force deflection (CFD) of the materials. Typically, CFD is determined experimentally by compressing a sample of a material until the sample is reduced to about 25% of its uncompressed size. The load applied to reach the 25% compression of the sample is then divided by the area of the sample over which the load is applied to arrive at the CFD. The CFD can also be measured by compressing a sample of a material to about 50% of the sample's uncompressed size. The CFD of a foam material can be a function of compression level, polymer stiffness, cell structure, foam density, and cell pore size. In some embodiments, the foam block 134 may have a CFD that is greater than a CFD of the tissue interface 108. For example, the tissue interface 108 may have a 25% CFD of about 2 kPa. The tissue interface 108 may compress to about 25% of its uncompressed size if a load of about 2 kPa is applied to the tissue interface 108. The foam block 134 may have a CFD of about 4 kPA. The foam block 134 may compress to about 25% of its uncompressed size if a load of about 4 kPa is applied to the foam block 134. Thus, the foam block 134 is more resistant to deformation than the tissue interface 108.

Furthermore, CFD can represent the tendency of a foam to return to its uncompressed state if a load is applied to compress the foam. For example, a foam having a CFD of about 4 kPa may exert about 4 kPa in reaction to 25% compression. The CFD of the foam block 134 may represent the ability of the foam block 134 to bias the film layer 132 toward an expanded position. For example, if the foam block 134 is compressed to 25% of its original size, the foam block 134 may exert a spring force that opposes the applied force over the area of the foam block 134 to which the force is applied. The reactive force may be proportional to the amount the foam block 134 is compressed.

The foam block 134 may have a free volume. The free volume of the foam block 134 may be the volume of free space of the foam block 134, for example, the volume of the plurality of channels of the foam block 134. In some embodiments, the free volume of the foam block 134 may be greater than the free volume of the sealed therapeutic environment. For example, the free volume of the foam block 134 may be greater than the free volume of the pouch 105. If the tissue interface 108 is used with the dressing assembly 102, the free volume of the foam block 134 may be greater than the combined free volume of the pouch 105 and the tissue interface 108. For example, if the free volume of the pouch 105 is 10 cm$^3$ and the free volume of the tissue interface is 10 cm$^3$, then the free volume of the foam block 134 may be greater than about 20 cm$^3$.

In some embodiments, the negative-pressure source 104 may be fluidly coupled to the cavity 111 through a fluid inlet, such as the tube 140. The tube 140 may be representative of a fluid communication path between the negative-pressure source 104 and the cavity 111. In other embodiments, the tube 140 may be a sealed channel or other fluid pathway. The tube 140 may include a lumen 142 fluidly coupled to the source cavity 138 and the pouch 105. In some embodiments, a valve, such as a check valve 144, may be fluidly coupled to the lumen 142. Exemplary check valves 144 may include ball check valves, diaphragm check valves, swing check valves, stop-check valves, duckbill valves, or pneumatic non-return valves. The check valve 144 may permit fluid communication from the pouch 105 to the source cavity 138 and prevent fluid communication from the source cavity 138 to the pouch 105. For example, if a pressure in the pouch 105 is greater than a pressure in the source cavity 138, the check valve 144 may open, and if the pressure in the source cavity 138 is greater than the pressure in the pouch 105, the check valve 144 may close.

In some embodiments, a filter may be disposed on an end of the tube 140. The filter may be a hydrophobic porous polymer filter having gel blocking properties. In some embodiments, the filter may be a non-gel blocking filter, such as a Gore MMT314 material having a polytetrafluoroethylene (PTFE) layer. The PTFE layer may face the manifolding structure to prevent fluid communication across the PTFE layer. In some embodiments, the filter may be on an end of the tube 140 proximate to the dressing assembly 102. In other embodiments, the filter may be on an end of the tube 140 proximate to the negative-pressure source 104.

The source cavity 138 may also be fluidly coupled to the ambient environment through a fluid outlet, such as the tube 146. For example, the tube 146 having a lumen 148 may fluidly couple the source cavity 138 to the ambient environment. The tube 146 may be representative of a fluid communication path between the ambient environment and the source cavity 138. A valve, such as a check valve 150, may be fluidly coupled to the lumen 148 to control fluid communication through the lumen 148. Exemplary check valves 150 may include ball check valves, diaphragm check valves, swing check valves, stop-check valves, duckbill valves, or pneumatic non-return valves. In some embodiments, the check valve 150 may permit fluid communication from the source cavity 138 to the ambient environment and prevent fluid communication from the ambient environment to the source cavity 138. For example, if a pressure in the source cavity 138 is greater than a pressure in the ambient environment, the check valve 150 may open, and if the pressure in the ambient environment is greater than the pressure in the source cavity 138, the check valve 150 may close.

In some embodiments, a filter may be disposed on an end of the tube 146. The filter may be a hydrophobic porous polymer filter having gel blocking properties. In some embodiments, the filter may be a non-gel blocking filter, such as a Gore MMT314 material having a polytetrafluoroethylene (PTFE) layer. The PTFE layer may face the manifolding structure to prevent fluid communication across the PTFE layer. In some embodiments, the filter may be on an end of the tube 146 proximate to the negative-pressure source 104. In other embodiments, the filter may be on an end of the tube 140 proximate to the ambient environment.

In some embodiments, the tissue interface 108 may be disposed adjacent to a tissue site. If the tissue interface 108 is used, the thickness of the tissue interface 108 may preferably be less than about 10 mm. The dressing assembly 102 may be disposed over the tissue interface 108 to create the sealed therapeutic environment. In some embodiments, the pouch 105 of the dressing assembly 102 may be positioned over the tissue interface 108 and the negative-pressure source 104 may be positioned over undamaged tissue proximate the tissue interface 108. A force, such as hand pressure, may be applied to the sealing flange 131 and the foundational flange 130, urging the bonding adhesive of the bonding adhesive layer 112 through the apertures 118 of the sealing adhesive layer 114 to form bonding couplings and securing the negative-pressure therapy system 100 to the tissue site.

Figure 2:
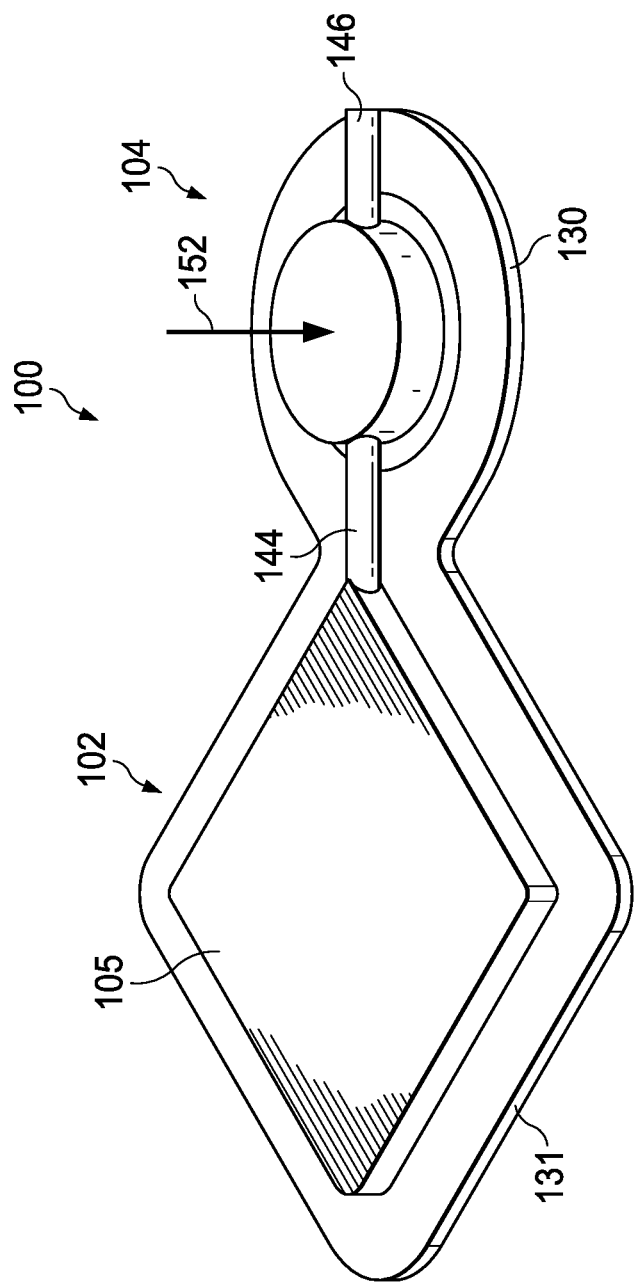
FIG. 2 is a top perspective view illustrating additional details that may be associated with an example embodiment of the negative-pressure therapy system of FIG. 1 in a first position.
Figure 3:
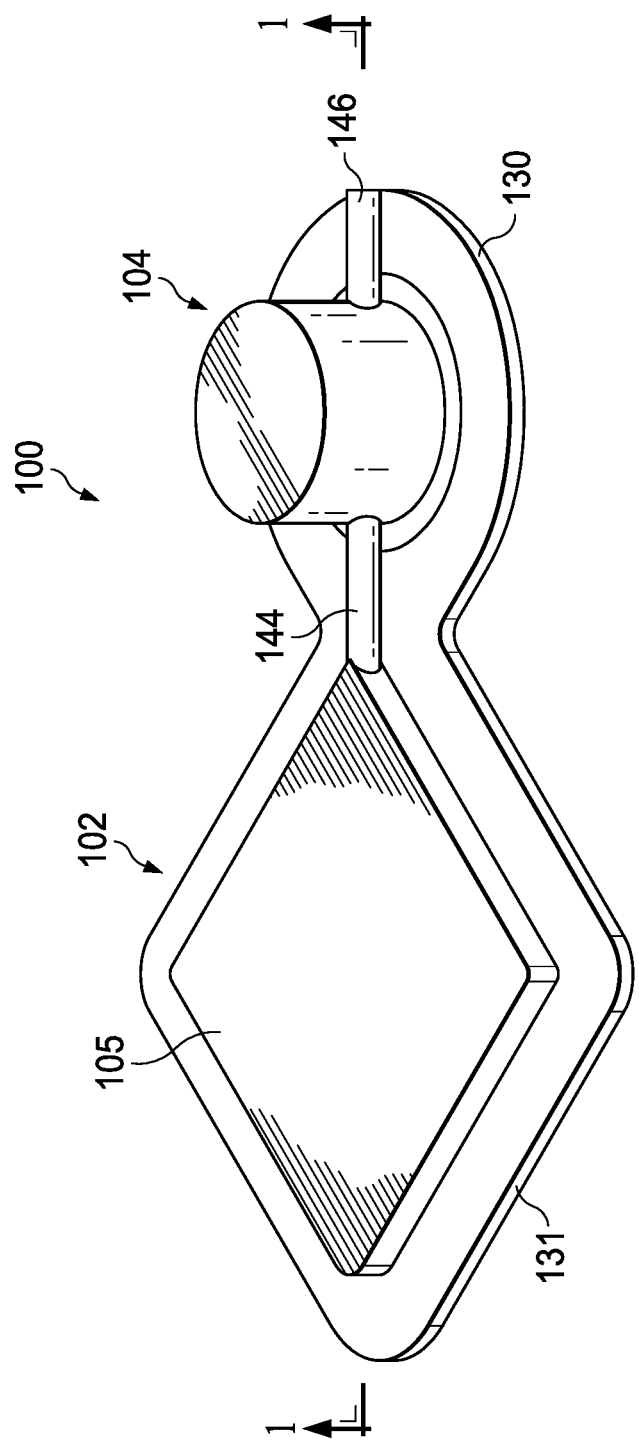
FIG. 3 is a top perspective view illustrating additional details that may be associated with an example embodiment of the negative-pressure therapy system of FIG. 1 in a second position.

FIG. 2 is a perspective view illustrating additional details of the negative-pressure source 104 in a first position, such as a collapsed position, and FIG. 3 is a perspective view illustrating additional details of the negative-pressure source 104 is a second position, such as an expanded position. Once positioned, the negative-pressure source 104 may be operated to generate a negative pressure in the pouch 105. As shown in FIG. 2, a force 152, such as hand pressure, may be applied to the film layer 132 over the foam block 134 to compress the foam block 134 to the first position and decrease the volume of the source cavity 138. If the foam block 134 and the source cavity 138 are fluidly isolated from the ambient environment, compression of the foam block 134 may increase the pressure in the source cavity 138. An increase of pressure in the source cavity 138 may create a pressure differential across the check valve 144 that urges the check valve 144 to close. Similarly, an increase of pressure in the source cavity 138 may create a pressure differential across the check valve 150 that urges the check valve 150 to open, allowing fluid from the source cavity 138 to flow through the tube 146 to the ambient environment. If the force 152 is removed, the foam block 134 may expand, increasing the volume of the source cavity 138 and decreasing the pressure in the source cavity 138. In response, the decrease in pressure in the source cavity 138 may create a pressure differential across the check valve 150 that urges the check valve 150 to close, preventing fluid from flowing from the ambient environment to the source cavity 138. The decrease in pressure in the source cavity 138 may also create a pressure differential across the check valve 144 that urges the check valve 144 to open, permitting fluid flow from the pouch 105 to the source cavity 138. Fluid may flow from the pouch 105 to the source cavity 138 until the source cavity 138 and the foam block 134 reach their respective uncompressed positions as shown in FIG. 3. In this manner, a portion of the total volume of fluid in the sealed therapeutic environment may be removed. In response to the removal of a portion of the fluid, a smaller volume of fluid occupies the sealed therapeutic environment, decreasing the pressure in the sealed therapeutic environment. Each time the foam block 134 is compressed and allowed to rebound, additional fluid may be removed from the sealed therapeutic environment, further decreasing the pressure.

Decreasing the pressure in the sealed therapeutic environment may create a pressure differential across the dressing assembly 102. If the pressure in the sealed therapeutic environment reaches the therapy pressure for negative-pressure therapy, the CFD of the foam block 134 may be insufficient to cause the foam block 134 to expand following compression of the foam block 134 from the second position of FIG. 3 to the first position of FIG. 2. The therapy pressure may be the pressure at which negative-pressure therapy may be performed. In some embodiments, the therapy pressure provided by the foam block 134 may be about 70 mm Hg of negative pressure. In other embodiments, the therapy pressure provided by the foam block 134 may be between about 50 mm Hg and 150 mm Hg of negative pressure. If the foam block 134 remains compressed as shown in FIG. 2, a patient or clinician may have an indication that the therapy pressure has been reached. The compressed foam block 134 may also act as a pressure reservoir. As negative-pressure therapy is provided, there may be a natural leakage or decline of negative pressure at the tissue site. As the negative pressure decreases in the sealed therapeutic environment, the pressure differential across the dressing assembly 102 may decrease and the foam block 134 may gradually expand, reapplying negative pressure at the tissue site. In some embodiments, the negative-pressure source 104 having the foam block 134 may maintain a therapeutic negative pressure for about 8 hours or more.

Figure 4:
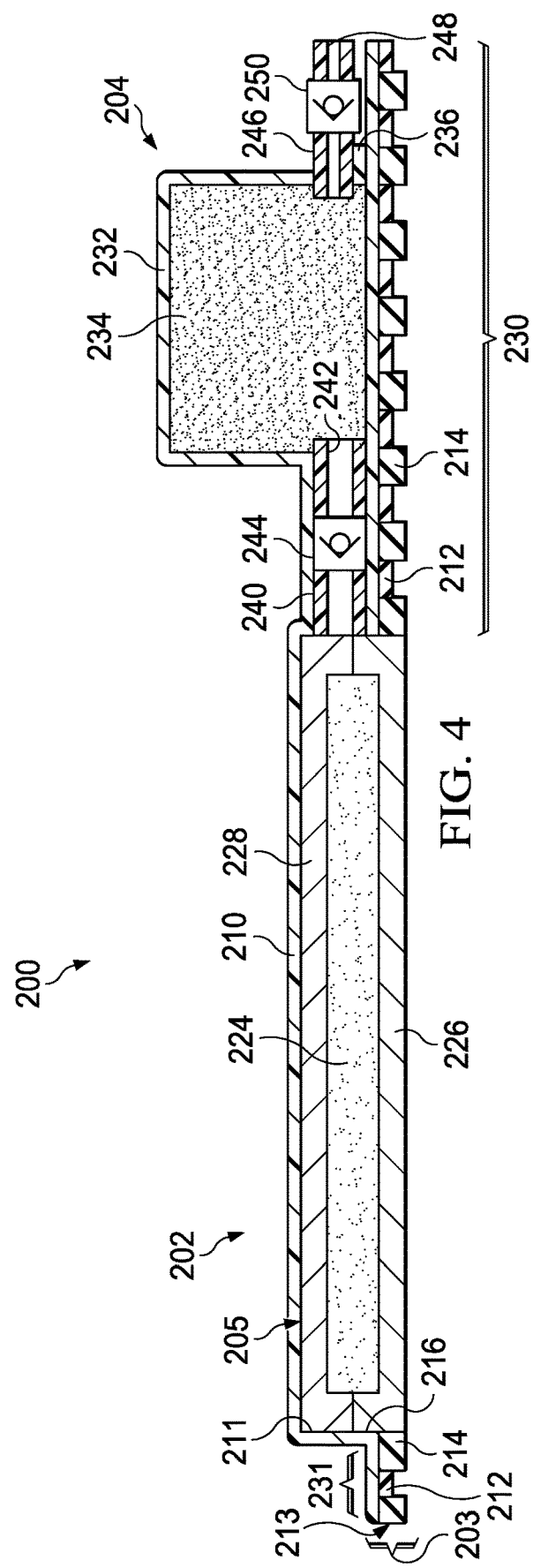
FIG. 4 is a sectional view of an example embodiment of another negative-pressure therapy system that can provide negative-pressure therapy in accordance with this specification.

FIG. 4 is a sectional view of an example embodiment of a negative-pressure therapy system 200 that can provide negative-pressure therapy in accordance with this specification. The negative-pressure therapy system 200 may be similar to and operate as described above with respect to the negative-pressure therapy system 100. Similar elements have similar reference numbers indexed to 200. As shown in FIG. 4, the negative-pressure therapy system 200 can include a dressing assembly 202 having a cover 203, a pouch 205, and a negative-pressure source 204. The cover 203, the pouch 205, and the negative-pressure source 204 may be coupled to each other. In some embodiments, the negative-pressure therapy system 200 can also include the tissue interface 108.

The pouch 205 may include an absorbent 224, a first outer layer, such as an upstream layer 226, and a second outer layer, such as a downstream layer 228. The upstream layer 226 and the downstream layer 228 may envelop or enclose the absorbent 224. The absorbent 224 may hold, stabilize, and/or solidify fluids that may be collected from the tissue site. The absorbent 224 may be of the type referred to as "hydrogels," "super-absorbents," or "hydrocolloids." If disposed within the dressing assembly 202, the absorbent 224 may be formed into fibers or spheres to manifold negative pressure until the absorbent 224 becomes saturated. Spaces or voids between the fibers or spheres may allow a negative pressure that is supplied to the dressing assembly 202 to be transferred within and through the absorbent 224 to the tissue site. In some exemplary embodiments, the absorbent 224 may be Texsus FP2325 having a material density of about 800 grams per square meter (gsm). In other exemplary embodiments, the absorbent material may be BASF 402C, Technical Absorbents 2317 available from Technical Absorbents (www.techabsorbents.com), sodium polyacrylate super absorbers, cellulosics (carboxy methyl cellulose and salts such as sodium CMC), or alginates.

In some exemplary embodiments, the absorbent 224 may be formed of granular absorbent components that may be scatter coated onto a paper substrate. Scatter coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate may be passed through a calender machine to provide a smooth uniform surface to the absorbent material.

In some exemplary embodiments, the upstream layer 226 and the downstream layer 228 have perimeter dimensions that may be larger than the perimeter dimensions of the absorbent 224 so that, if the absorbent 224 is positioned between the upstream layer 226 and the downstream layer 228 and the center portions of the absorbent 224, the upstream layer 226, and the downstream layer 228 are aligned, the upstream layer 226 and the downstream layer 228 may extend beyond the perimeter of the absorbent 224. In some exemplary embodiments, the upstream layer 226 and the downstream layer 228 surround the absorbent 224. Peripheral portions of the upstream layer 226 and the downstream layer 228 may be coupled so that the upstream layer 226 and the downstream layer 228 enclose the absorbent 224. The upstream layer 226 and the downstream layer 228 may be coupled by high frequency welding, ultrasonic welding, heat welding, or impulse welding, for example. In other exemplary embodiments, the upstream layer 226 and the downstream layer 228 may be coupled by bonding or folding, for example.

The upstream layer 226 may be formed of non-woven material in some embodiments. For example, the upstream layer 226 may have a polyester fibrous porous structure. The upstream layer 226 may be porous, but preferably the upstream layer 226 is not perforated. The upstream layer 226 may have a material density between about 80 gsm and about 150 gsm. In other exemplary embodiments, the material density may be lower or greater depending on the particular application of the pouch 205. In some embodiments, the upstream layer 226 may a plurality of layers of, for example, non-woven material. The upstream layer 226 may be formed of Libeltex TDL2, for example. In other embodiments, the upstream layer 226 may also be formed of Libeltex TL4. The upstream layer 226 may have a hydrophilic side and a hydrophobic side.

The downstream layer 228 may also be formed of a non-woven material in some embodiments. For example, the downstream layer 228 may have a polyester fibrous porous structure. The downstream layer 228 may be porous, but the downstream layer 228 preferably is not perforated. The downstream layer 228 may have a material density between about 80 gsm and about 150 gsm. In other exemplary embodiments, the material density may be lower or greater depending on the particular application of the pouch 205. The material density of the downstream layer 228 may be greater or less than the material density of the upstream layer 226. In some embodiments, a thickness of the downstream layer 228 may be greater than a thickness of the upstream layer 226. In other embodiments, the thickness of the downstream layer 228 may be less than the thickness of the upstream layer 226. In some embodiments, the downstream layer 228 may a plurality of layers of, for example, non-woven material. The downstream layer 228 may be formed of Libeltex TL4. In other exemplary embodiments, the downstream layer 228 may be formed of Libeltex TDL2.

The upstream layer 226 and the downstream layer 228 may be manifolding layers configured to facilitate fluid movement through the pouch 205. In some embodiments, the upstream layer 226 and the downstream layer 228 may each have a hydrophobic side and a hydrophilic side. The hydrophobic side may also be referred to as a wicking side, wicking surface, distribution surface, distribution side, or fluid distribution surface. The hydrophobic side may be a smooth distribution surface configured to move fluid along a grain of the upstream layer 226 and the downstream layer 228, distributing fluid throughout the upstream layer 226 and the downstream layer 228. The hydrophilic side may be configured to acquire bodily fluid from the hydrophobic side to aid in bodily fluid movement into the absorbent 224. The hydrophilic side may also be referred to as a fluid acquisition surface, fluid acquisition side, hydrophilic acquisition surface, or hydrophilic acquisition side. The hydrophilic side may be a fibrous surface and be configured to draw fluid into the upstream layer 226 and the downstream layer 228. In some embodiments, the hydrophilic side of the upstream layer 226 and the downstream layer 228 may be positioned adjacent to the absorbent 224. In other embodiments, the hydrophobic side of the upstream layer 226 and the downstream layer 228 may be positioned adjacent to the absorbent 224. In still other embodiments, the hydrophilic side of one of the upstream layer 226 or the downstream layer 228 may be positioned adjacent to the absorbent 224, and the hydrophobic side of the other of the upstream layer 226 or the downstream layer 228 may be positioned adjacent to the absorbent 224.

In some embodiments, the cover 203 may include a barrier layer 210 and an adhesive layer 213 having a bonding adhesive 212 and a sealing adhesive 214. The barrier layer 210 may be formed from a range of medically approved films ranging in thickness from about 15 microns (μm) to about 50 microns (μm). The barrier layer 210 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the barrier layer 210 may be formed from a breathable cast matt polyurethane film sold by Expopack Advanced Coatings of Wrexham, United Kingdom, under the name INSPIRE 2301.

The barrier layer 210 may have a high moisture vapor transmission rate (MVTR). The MVTR of the barrier layer 210 allows vapor to egress and inhibits liquids from exiting. In some embodiments, the MVTR of the barrier layer 210 may be greater than or equal to 300 g/m$^2$/24 hours. In other embodiments, the MVTR of the barrier layer 210 may be greater than or equal to 1000 g/m$^2$/24 hours. The illustrative INSPIRE 2301 film may have an MVTR (inverted cup technique) of 14400 g/m$^2$/24 hours and may be approximately 30 microns thick. In other embodiments, a drape having a low MVTR or that allows no vapor transfer might be used. The barrier layer 210 can also function as a barrier to liquids and microorganisms.

In some embodiments, the barrier layer 210 may be adapted to form a cavity 211. For example, the barrier layer 210 may be placed on a mold and stretched to plastically deform a portion of the barrier layer 210, forming the cavity 211. A periphery of the barrier layer 210 that is not stretched by the formation of the cavity 211 may form a flange surrounding the cavity 211. In some embodiments, the cavity 211 may be positioned so that a portion of the flange may be larger on a first side of the cavity 211 than on a second side of the cavity 211. The disparity in sizes of the flange may form a foundational flange 230 and a sealing flange 231. In some embodiments, the pouch 205 may be disposed in the cavity 211. The cavity 211 may also be a portion of the barrier layer 210 that is free of the adhesive layer 213. For example, during manufacturing, a portion of the barrier layer 210 may be left without the adhesive layer 213; the area of the barrier layer 210 without the adhesive layer 213 may be equal to a surface area of the pouch 205 to be covered by the barrier layer 210.

The foundational flange 230 may extend away from the cavity 211. In some embodiments, the foundational flange 230 may have a length sufficient to permit other objects to be coupled to the dressing assembly 202. In some embodiments, the foundational flange 230 may support the negative-pressure source 204, as illustrated in FIG. 4.

The adhesive layer 213 may be coupled to the barrier layer 210 on a side of the barrier layer 210 having an opening of the cavity 211. In some embodiments, the adhesive layer 213 may include an aperture 216. The aperture 216 may be coextensive with the opening of the cavity 211. For example, the adhesive layer 213 may cover the barrier layer 210 at the foundational flange 230 and the sealing flange 231, leaving the portion of the barrier layer 210 forming the cavity 211 free of the adhesive layer 213.

In some embodiments, the bonding adhesive 212 may be deposited onto the barrier layer 210 in a pattern. For example, the bonding adhesive 212 may be applied to the barrier layer 210 on a side of the barrier layer 210 having the opening of the cavity 211 so that the bonding adhesive 212 forms a checkerboard pattern. The barrier layer 210 may have portions having the bonding adhesive 212 deposited thereon and portions that may be free of the bonding adhesive 212.

The sealing adhesive 214 may also be deposited onto the barrier layer 210 in a pattern. For example, the sealing adhesive 214 may be applied to the barrier layer 210 on the side of the barrier layer 210 having the opening of the cavity 211 so that the sealing adhesive 214 forms a checkerboard pattern. The barrier layer 210 may have portions having the sealing adhesive 214 deposited thereon and portions that may be free of the sealing adhesive 214.

The pattern of the bonding adhesive 212 and the pattern of the sealing adhesive 214 may be registered. Registration of the bonding adhesive 212 and the sealing adhesive 214 generally refers to the alignment of the two adhesives relative to one another. In particular, registration of the bonding adhesive 212 and the sealing adhesive 214 may refer to the coordination of adhesive placement on the barrier layer 210 to achieve a desired effect. For example, a certain percentage of overlap of one adhesive over the other adhesive, minimal overlap of one adhesive over the other adhesive so that the adhesives are offset from one another, or complete overlap of one adhesive over the other adhesive are all adhesive placements that may be considered registered. For example, the bonding adhesive 212 and the sealing adhesive 214 may be registered by being disposed on the barrier layer 210 so that the bonding adhesive 212 and the sealing adhesive 214 each substantially couple to the barrier layer 210. In addition, the bonding adhesive 212 and the sealing adhesive 214 of the example may be aligned relative to one another to have minimal overlap of one adhesive over the other adhesive. In another example, the sealing adhesive 214 may be offset from the bonding adhesive 212, with both adhesives being coupled to the barrier layer 210. Registering the bonding adhesive 212 and the sealing adhesive 214 provides for easier manufacturing and use of the cover 203. Registering of the bonding adhesive 212 and the sealing adhesive 214 may also enhance desired properties of the cover 203.

The bonding adhesive 212 may comprise an acrylic adhesive, rubber adhesive, high-tack silicone adhesive, polyurethane, or other substance. In an illustrative example, the bonding adhesive 212 comprises an acrylic adhesive with coating weight of 15 grams/m$^2$ (gsm) to 70 grams/m$^2$ (gsm). In some embodiments, the bond strength of the bonding adhesive may have a peel adhesion or resistance to being peeled from a stainless steel material between about 6N/25 mm to about 10N/25 mm on stainless steel substrate at 23° C. at 50% relative humidity based on the American Society for Testing and Materials ("ASTM") standard ASTM D3330. The bonding adhesive 212 may be about 30 microns to about 60 microns in thickness.

The sealing adhesive 214 may comprise a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 30 gsm-70 gsm acrylic), polyurethane, polyolefin, or hydrogenated styrenic copolymers. The sealing adhesive 214 may have a thickness in the range of about 100 microns (µm) to about 1000 microns (µm). In some embodiments, the sealing adhesive 214 may have stiffness between about 5 Shore OO and about 80 Shore OO. The sealing adhesive 214 may be hydrophobic or hydrophilic. The sealing adhesive 214 may be an adhesive having a low to medium tackiness, for example, a silicone polymer, polyurethane, or an additional acrylic adhesive. In some embodiments, the bond strength of the sealing adhesive may have a peel adhesion or resistance to being peeled from a stainless steel material between about 0.5N/25 mm to about 1.5N/25 mm on stainless steel substrate at 23° C. at 50% relative humidity based on ASTM D3330. The sealing adhesive 214 may have a tackiness such that the sealing adhesive 214 may achieve the bond strength above after a contact time of less than 60 seconds. Tackiness may be considered a bond strength of an adhesive after a very low contact time between the adhesive and a substrate. In some embodiments, the sealing adhesive 214 may have a tackiness that may be about 30% to about 50% of the tackiness of the bonding adhesive of the bonding adhesive 212.

In the assembled state, the adhesive layer 213 may be coupled to the sealing flange 231 and the foundational flange 230. In some embodiments, the thickness of the bonding adhesive 212 may be less than the thickness of the sealing adhesive 214 so that the adhesive layer 213 may have a varying thickness. If the adhesive layer 213 is placed proximate to or in contact with the epidermis of the patient, the sealing adhesive 214 may be in contact with the epidermis to form sealing couplings. In some embodiments, the thickness of the bonding adhesive 212 may be less than the thickness of the sealing adhesive 214, forming a gap between the bonding adhesive 212 and the epidermis.

The initial tackiness of the sealing adhesive 214 is preferably sufficient to initially couple the sealing adhesive 214 to the epidermis by forming sealing couplings. Once in the desired location, a force can be applied to the barrier layer 210 of the cover 203. For example, the user may rub the foundational flange 230 and the sealing flange 231. This action can cause at least a portion of the bonding adhesive 212 to be forced into the plurality of apertures 218 and into contact with the epidermis to form bonding couplings. The bonding couplings provide secure, releasable mechanical fixation to the epidermis.

As illustrated in FIG. 4, the negative-pressure source 204, which may also be referred to as a blister, may be coupled to the barrier layer 210 of the foundational flange 230. The negative-pressure source 204 may be an enclosure formed by a film layer 232 and having a foam block 234 disposed therein. In some embodiments, the film layer 232 may form a source flange 236 and a source cavity 238. The source cavity 238 may be a portion of the film layer 232 this is plastically stretched, such as by vacuum forming, thermoforming, micro-thermoforming, injection molding, or blow molding, for example. In some embodiments, the source cavity 238 may form walls of the negative-pressure source 204 that may be resilient or flexible. The source flange 236 may be a portion of the film layer 232 adjacent to and surrounding an opening of the source cavity 238. In some embodiments, the foam block 234 may be disposed in the source cavity 238. The source flange 236 may be coupled to the barrier layer 210 of the foundational flange 230 to seal the foam block 234 in the source cavity 238. In some embodiments, the source flange 236 may be coupled to the barrier layer 210 by high frequency welding, ultrasonic welding, heat welding, or impulse welding, for example. In other exemplary embodiments, the source flange 236 may be coupled to the barrier layer 210 by bonding or folding, for example. In some embodiments, if the source flange 236 is coupled to the barrier layer 210 of the foundational flange 230, the source cavity 238 may be fluidly isolated from the ambient environment and the pouch 205.

The film layer 232 may be constructed from a material that can provide a fluid seal between two components or two environments, such as between the source cavity 238 and a local external environment, while allowing for repeated elastic deformation of the film layer 232. The film layer 232 may be, for example, an elastomeric film or membrane that can provide a seal between the source cavity 238 and the ambient environment. In some example embodiments, the film layer 232 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In an exemplary embodiment, the film layer 232 may be a polyurethane having a thickness between about 50 microns and about 250 microns and preferably about 100 microns.

The foam block 234 may be a foam having a plurality of interconnected flow channels. For example, cellular foam, open-cell foam, reticulated foam, porous tissue collections, and other porous material that generally include pores, edges, and/or walls adapted to form interconnected fluid pathways. Liquids, gels, and other foams may also include or be cured to include apertures and flow channels. In some illustrative embodiments, the foam block 234 may be a porous foam material having interconnected cells or pores adapted to uniformly (or quasi-uniformly) distribute fluid throughout the foam block 234. The foam material may be either hydrophobic or hydrophilic. In one non-limiting example, the foam block 234 may be an open-cell, reticulated polyurethane foam such as GranuFoam® dressing available from Kinetic Concepts, Inc. of San Antonio, Tex. Another exemplary embodiment of the foam block 234 may be Z48AA foam from FXI®.

Foam materials may have an elastic modulus, which may also be referred to as a foam modulus. Generally, the elastic modulus of a material may measure the resistance of the material to elastic deformation under a load. The elastic modulus of a material may be defined as the slope of a stress-strain curve in the elastic deformation region of the curve. The elastic deformation region of a stress-strain curve represents that portion of the curve where a deformation of a material due to an applied load is elastic, that is, not permanent. If the load is removed, the material may return to its pre-loaded state. Stiffer materials may have a higher elastic modulus, and more compliant materials may have a lower elastic modulus. Generally, references to the elastic modulus of a material refers to a material under tension.

For some materials under compression, the elastic modulus can be compared between materials by comparing the compression force deflection (CFD) of the materials. Typically, CFD is determined experimentally by compressing a sample of a material until the sample is reduced to about 25% of its uncompressed size. The load applied to reach the 25% compression of the sample is then divided by the area of the sample over which the load is applied to arrive at the CFD. The CFD can also be measured by compressing a sample of a material to about 50% of the sample's uncompressed size. The CFD of a foam material can be a function of compression level, polymer stiffness, cell structure, foam density, and cell pore size. The foam block 234 may have a CFD of about 4 kPA. The foam block 234 may compress to about 25% of its uncompressed size if a load of about 4 kPa is applied to the foam block 234.

Furthermore, CFD can represent the tendency of a foam to return to its uncompressed state if a load is applied to compress the foam. For example, a foam having a CFD of about 4 kPa may exert about 4 kPa in reaction to 25% compression. The CFD of the foam block 234 may represent the ability of the foam block 234 to bias the film layer 232 toward an expanded position. For example, if the foam block 234 is compressed to 25% of its original size, the foam block 234 may exert a spring force that opposes the applied force over the area of the foam block 234 to which the force is applied. The reactive force may be proportional to the amount the foam block 234 is compressed.

The foam block 234 may have a free volume. The free volume of the foam block 234 may be the volume of free space of the foam block 234, for example, the volume of the plurality of channels of the foam block 234. In some embodiments, the free volume of the foam block 234 may be greater than the free volume of the sealed therapeutic environment. For example, the free volume of the foam block 234 may be greater than the free volume of the pouch 205. If the free volume of the pouch 205 is about 10 cm$^3$, then the free volume of the foam block 234 may be greater than about 10 cm$^3$.

In some embodiments, the negative-pressure source 204 may be fluidly coupled to the cavity 211 through a fluid inlet, such as a tube 240. The tube 240 may be representative of a fluid communication path between the negative-pressure source 204 and the cavity 211. In other embodiments, the tube 240 may be a sealed channel or other fluid pathway. The tube 240 may include a lumen 242 fluidly coupled to the source cavity 238 and the pouch 205. In some embodiments, a valve, such as a check valve 244, may be fluidly coupled to the lumen 242. Exemplary check valves 244 may include ball check valves, diaphragm check valves, swing check valves, stop-check valves, duckbill valves, or pneumatic non-return valves. The check valve 244 may permit fluid communication from the pouch 205 to the source cavity 238 and prevent fluid communication from the source cavity 238 to the pouch 205. For example, if a pressure in the pouch 205 is greater than a pressure in the source cavity 238, the check valve 244 may open, and if the pressure in the source cavity 238 is greater than the pressure in the pouch 205, the check valve 244 may close. In some embodiments, a filter may be disposed on an end of the tube 240. The filter may be a hydrophobic porous polymer filter having gel blocking properties.

The source cavity 238 may also be fluidly coupled to the ambient environment through a fluid outlet, such as a tube 246. The tube 246 may be representative of a fluid communication path between the ambient environment and the source cavity 238. For example, the tube 246 having a lumen 248 may fluidly couple the source cavity 238 to the ambient environment. A valve, such as a check valve 250, may be fluidly coupled to the lumen 248 to control fluid communication through the lumen 248. Exemplary check valves 250 may include ball check valves, diaphragm check valves, swing check valves, stop-check valves, duckbill valves, or pneumatic non-return valves. In some embodiments, the check valve 250 may permit fluid communication from the source cavity 238 to the ambient environment and prevent fluid communication from the ambient environment to the source cavity 238. For example, if a pressure in the source cavity 238 is greater than a pressure in the ambient environment, the check valve 250 may open, and if the pressure in the ambient environment is greater than the pressure in the source cavity 238, the check valve 250 may close. In some embodiments, a filter may be disposed on an end of the tube 246. The filter may be a hydrophobic porous polymer filter having gel blocking properties.

Figure 5:
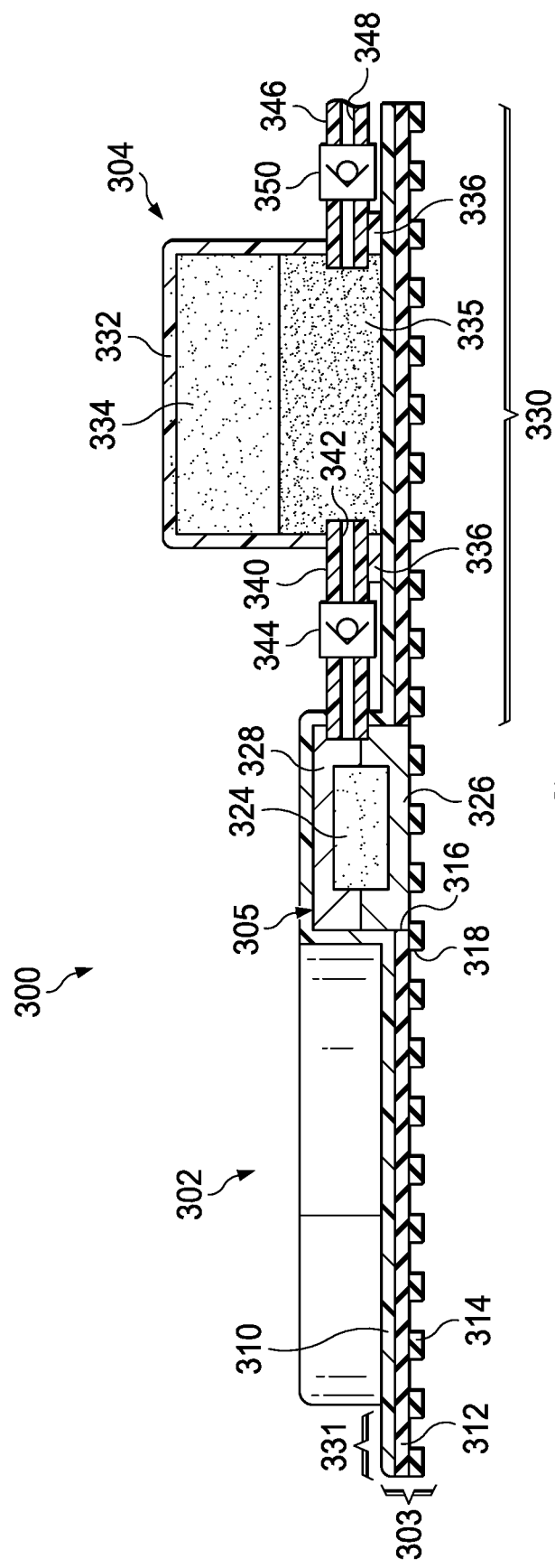
FIG. 5 is a sectional view of an example embodiment of another negative-pressure therapy system that can provide negative-pressure therapy in accordance with this specification.

FIG. 5 is a sectional view of an example embodiment of a negative-pressure therapy system 300 that can provide negative-pressure therapy in accordance with this specification. The negative-pressure therapy system 300 may be similar to and operate as described above with respect to the negative-pressure therapy system 100. Similar elements have similar reference numbers indexed to 300. As shown in FIG. 5, the negative-pressure therapy system 300 can include a dressing assembly 302 having a cover 303, a pouch 305, and a negative-pressure source 304. The cover 303, the pouch 305, and the negative-pressure source 304 may be coupled to each other. In some embodiments, the negative-pressure therapy system 300 can also include the tissue interface 108.

The pouch 305 may include an absorbent 324, a first outer layer, such as an upstream layer 326, and a second outer layer, such as a downstream layer 328. The upstream layer 326 and the downstream layer 328 may envelop or enclose the absorbent 324. The absorbent 324 may hold, stabilize, and/or solidify fluids that may be collected from the tissue site. The absorbent 324 may be formed from materials referred to as "hydrogels," "super-absorbents," or "hydrocolloids." If disposed within the dressing assembly 302, the absorbent 324 may be formed into fibers or spheres to manifold negative pressure until the absorbent 324 becomes saturated. Spaces or voids between the fibers or spheres may allow a negative pressure that is supplied to the dressing assembly 302 to be transferred within and through the absorbent 324 to the tissue site. In some exemplary embodiments, the absorbent 324 may be Texsus FP2325 having a material density of about 800 grams per square meter (gsm). In other exemplary embodiments, the absorbent material may be BASF 402C, Technical Absorbents 2317 available from Technical Absorbents (www.techabsorbents.com), sodium polyacrylate super absorbers, cellulosics (carboxy methyl cellulose and salts such as sodium CMC), or alginates.

In some exemplary embodiments, the absorbent 324 may be formed of granular absorbent components that may be scatter coated onto a paper substrate. Scatter coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate may be passed through a calender machine to provide a smooth uniform surface to the absorbent material.

In some exemplary embodiments, the upstream layer 326 and the downstream layer 328 have perimeter dimensions that may be larger than the perimeter dimensions of the absorbent 324 so that, if the absorbent 324 is positioned between the upstream layer 326 and the downstream layer 328 and the center portions of the absorbent 324, the upstream layer 326, and the downstream layer 328 are aligned, the upstream layer 326 and the downstream layer 328 may extend beyond the perimeter of the absorbent 324. In some exemplary embodiments, the upstream layer 326 and the downstream layer 328 surround the absorbent 324. Peripheral portions of the upstream layer 326 and the downstream layer 328 may be coupled so that the upstream layer 326 and the downstream layer 328 enclose the absorbent 324. The upstream layer 326 and the downstream layer 328 may be coupled by high frequency welding, ultrasonic welding, heat welding, or impulse welding, for example. In other exemplary embodiments, the upstream layer 326 and the downstream layer 328 may be coupled by bonding or folding, for example.

The upstream layer 326 may be formed of non-woven material in some embodiments. For example, the upstream layer 326 may have a polyester fibrous porous structure. The upstream layer 326 may be porous, but preferably the upstream layer 326 is not perforated. The upstream layer 326 may have a material density between about 80 gsm and about 150 gsm. In other exemplary embodiments, the material density may be lower or greater depending on the particular application of the pouch 305. In some embodiments, the upstream layer 326 may a plurality of layers of, for example, non-woven material. The upstream layer 326 may be formed of Libeltex TDL2, for example. In other embodiments, the upstream layer 326 may also be formed of Libeltex TL4. The upstream layer 326 may have a hydrophilic side and a hydrophobic side.

The downstream layer 328 may also be formed of a non-woven material in some embodiments. For example, the downstream layer 328 may have a polyester fibrous porous structure. The downstream layer 328 may be porous, but the downstream layer 328 preferably is not perforated. The downstream layer 328 may have a material density between about 80 gsm and about 150 gsm. In other exemplary embodiments, the material density may be lower or greater depending on the particular application of the pouch 305. The material density of the downstream layer 328 may be greater or less than the material density of the upstream layer 326. In some embodiments, a thickness of the downstream layer 328 may be greater than a thickness of the upstream layer 326. In other embodiments, the thickness of the downstream layer 328 may be less than the thickness of the upstream layer 326. In some embodiments, the downstream layer 328 may a plurality of layers of, for example, non-woven material. The downstream layer 328 may be formed of Libeltex TL4. In other embodiments, the downstream layer 328 may be formed of Libeltex TDL2.

The upstream layer 326 and the downstream layer 328 may be manifolding layers configured to facilitate fluid movement through the pouch 305. In some embodiments, the upstream layer 326 and the downstream layer 328 may each have a hydrophobic side and a hydrophilic side. The hydrophobic side may also be referred to as a wicking side, wicking surface, distribution surface, distribution side, or fluid distribution surface. The hydrophobic side may be a smooth distribution surface configured to move fluid along a grain of the upstream layer 326 and the downstream layer 328, distributing fluid throughout the upstream layer 326 and the downstream layer 328. The hydrophilic side may be configured to acquire bodily fluid from the hydrophobic side to aid in bodily fluid movement into the absorbent 324. The hydrophilic side may also be referred to as a fluid acquisition surface, fluid acquisition side, hydrophilic acquisition surface, or hydrophilic acquisition side. The hydrophilic side may be a fibrous surface and be configured to draw fluid into the upstream layer 326 and the downstream layer 328. In some embodiments, the hydrophilic side of the upstream layer 326 and the downstream layer 328 may be positioned adjacent to the absorbent 324. In other embodiments, the hydrophobic side of the upstream layer 326 and the downstream layer 328 may be positioned adjacent to the absorbent 324. In still other embodiments, the hydrophilic side of one of the upstream layer 326 or the downstream layer 328 may be positioned adjacent to the absorbent 324, and the hydrophobic side of the other of the upstream layer 326 or the downstream layer 328 may be positioned adjacent to the absorbent 324.

In some embodiments, the cover 303 may include or may be a hybrid drape that includes a barrier layer 310, a bonding adhesive layer 312, and a sealing adhesive layer 314. The barrier layer 310 may be formed from a range of medically approved films ranging in thickness from about 15 microns ($\mu$m) to about 50 microns ($\mu$m). The barrier layer 310 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the barrier layer 310 may be formed from a breathable cast matt polyurethane film sold by Expopack Advanced Coatings of Wrexham, United Kingdom, under the name INSPIRE 2301.

The barrier layer 310 may have a high moisture vapor transmission rate (MVTR). The MVTR of the barrier layer 310 allows vapor to egress and inhibits liquids from exiting. In some embodiments, the MVTR of the barrier layer 310 may be greater than or equal to 300 g/m$^2$/24 hours. In other embodiments, the MVTR of the barrier layer 310 may be greater than or equal to 1000 g/m$^2$/24 hours. The illustrative INSPIRE 2301 film may have an MVTR (inverted cup technique) of 14400 g/m$^2$/24 hours and may be approximately 30 microns thick. In other embodiments, a drape having a low MVTR or that allows no vapor transfer might be used. The barrier layer 310 can also function as a barrier to liquids and microorganisms.

In some embodiments, the barrier layer 310 may be adapted to form a bulge on a first side of the barrier layer 310 and a cavity 311 on an opposite side of the barrier layer 310. For example, the barrier layer 310 may be placed on a mold and stretched to plastically deform a portion of the barrier layer 310, forming the cavity 311. A periphery of the barrier layer 310 that is not stretched by the formation of the cavity 311 may form a flange surrounding the cavity 311. In some embodiments, the cavity 311 may be positioned so that a portion of the flange may be larger on a first side of the cavity 311 than on a second side of the cavity 311. The disparity in sizes of the flange may form a foundational flange 330 and a sealing flange 331. In some embodiments, the pouch 305 may be disposed in the cavity 311. The cavity 311 may also be a portion of the barrier layer 310 that is free of the bonding adhesive layer 312. For example, during manufacturing, a portion of the barrier layer 310 may be left without the bonding adhesive layer 312; the area of the barrier layer 310 without the bonding adhesive layer 312 may be equal to a surface area of the pouch 305 to be covered by the barrier layer 310.

The foundational flange 330 may extend away from the cavity 311. In some embodiments, the foundational flange 330 may have a length and a width sufficient to permit other objects to be coupled to the dressing assembly 302. In some embodiments, the foundational flange 330 may support the negative-pressure source 304, as illustrated in FIG. 5.

The bonding adhesive layer 312 may be coupled to the barrier layer 310 on a side of the barrier layer 310 having an opening of the cavity 311. In some embodiments, the bonding adhesive layer 312 may include an aperture 316. The aperture 316 may be coextensive with the opening of the cavity 311. For example, the bonding adhesive layer 312 may cover the barrier layer 310 at the foundational flange 330 and the sealing flange 331, leaving the portion of the barrier layer 310 forming the cavity 311 free of bonding adhesive.

The bonding adhesive layer 312 may comprise an acrylic adhesive, rubber adhesive, high-tack silicone adhesive, polyurethane, or other substance. In an illustrative example, the bonding adhesive layer 312 comprises an acrylic adhesive with coating weight of 15 grams/m$^2$ (gsm) to 70 grams/m$^2$ (gsm). The bonding adhesive layer 312 may be a continuous layer of material or may be a layer with apertures (not shown). The apertures may be formed after application of the bonding adhesive layer 312 or may be formed by coating the bonding adhesive layer 312 in patterns on a carrier layer. In some embodiments, the bond strength of the bonding adhesive may have a peel adhesion or resistance to being peeled from a stainless steel material between about 6N/25 mm to about 10N/25 mm on stainless steel substrate at 23° C. at 50% relative humidity based on the American Society for Testing and Materials ("ASTM") standard ASTM D3330. The bonding adhesive layer 312 may be about 30 microns to about 60 microns in thickness.

The sealing adhesive layer 314 may be coupled to the bonding adhesive layer 312 and the pouch 305. For example, the sealing adhesive layer 314 may cover the sealing flange 331, the pouch 305, and the foundational flange 330. The sealing adhesive layer 314 may be formed with the plurality of apertures 318. The apertures 318 may be numerous shapes, for example, circles, squares, stars, ovals, polygons, slits, complex curves, rectilinear shapes, triangles, or other shapes. Each aperture 318 of the plurality of apertures 318 may have an effective diameter, which is the diameter of a circular area having the same surface area as the aperture 318. The average effective diameter of each aperture 318 may typically be in the range of about 6 mm to about 50 mm. The plurality of apertures 318 may have a uniform pattern or may be randomly distributed in the sealing adhesive layer 314. Generally, the apertures 318 may be disposed across a length and width of the sealing adhesive layer 314.

The sealing adhesive layer 314 may comprise a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 30 gsm-70 gsm acrylic), polyurethane, polyolefin, or hydrogenated styrenic copolymers. The sealing adhesive layer 314 may have a thickness in the range of about 100 microns (μm) to about 1000 microns (μm). In some embodiments, the sealing adhesive layer 314 may have stiffness between about 5 Shore OO and about 80 Shore OO. The sealing adhesive layer 314 may be hydrophobic or hydrophilic. The sealing adhesive of the sealing adhesive layer 314 may be an adhesive having a low to medium tackiness, for example, a silicone polymer, polyurethane, or an additional acrylic adhesive. In some embodiments, the bond strength of the sealing adhesive may have a peel adhesion or resistance to being peeled from a stainless steel material between about 0.5N/25 mm to about 1.5N/25 mm on stainless steel substrate at 23° C. at 50% relative humidity based on ASTM D3330. The sealing adhesive of the sealing adhesive layer 314 may have a tackiness such that the sealing adhesive may achieve the bond strength above after a contact time of less than 60 seconds. Tackiness may be considered a bond strength of an adhesive after a very low contact time between the adhesive and a substrate. In some embodiments, the sealing adhesive layer 314 may have a tackiness that may be about 30% to about 50% of the tackiness of the bonding adhesive of the bonding adhesive layer 312.

In the assembled state, the bonding adhesive layer 312 may be coupled to the barrier layer 310. The sealing adhesive layer 314 may be coupled to the bonding adhesive layer 312 at the sealing flange 331 and the foundational flange 330 and to the pouch 305 at the cavity 311. In some embodiments, a scrim layer may be disposed in the sealing adhesive layer 314. The scrim layer may provide additional mechanical support for the sealing adhesive layer 314. In some embodiments, the sealing adhesive layer 314 may be treated on a portion and a side of the sealing adhesive layer 314 adjacent to the pouch 305. The treated portion of the sealing adhesive layer 314 may reduce the tackiness of the sealing adhesive layer 314 so that the sealing adhesive layer 314 may not readily adhere to the pouch 305. The initial tackiness of the sealing adhesive layer 314 is preferably sufficient to initially couple the sealing adhesive layer 314 to the epidermis by forming sealing couplings. Once in the desired location, a force can be applied to the barrier layer 310 of the cover 303. For example, the user may rub the foundational flange 330 and the sealing flange 331. This action can cause at least a portion of the bonding adhesive layer 312 to be forced into the plurality of apertures 318 and into contact with the epidermis to form bonding couplings. The bonding couplings provide secure, releasable mechanical fixation to the epidermis.

The average effective diameter of the plurality of apertures 318 for the sealing adhesive layer 314 may be varied as one control of the tackiness or adhesion strength of the cover 303. In this regard, there is interplay between three main variables for each embodiment: the thickness of the sealing adhesive layer 314, the average effective diameter of the plurality of apertures 318, and the tackiness of the bonding adhesive layer 312. The more bonding adhesive of the bonding adhesive layer 312 that extends through the apertures 318, the stronger the bond of the bonding coupling. The thinner the sealing adhesive layer 314, the more bonding adhesive of the bonding adhesive layer 312 generally extends through the apertures 318 and the greater the bond of the bonding coupling. As an example of the interplay, if a very tacky bonding adhesive layer 312 is used and the thickness of the sealing adhesive layer 314 is small, the average effective diameter of the plurality of apertures 318 may be relatively smaller than apertures 318 in a thicker sealing adhesive layer 314 and less tacky bonding adhesive layer 312. In some embodiments, the thickness of the sealing adhesive layer 314 may be approximately 200 microns, the thickness of the bonding adhesive layer 312 is approximately 30 microns with a tackiness of 2000 g/25 cm wide strip, and the average effective diameter of each aperture 318 is approximately about 6 mm.

As illustrated in FIG. 5, the negative-pressure source 304, which may also be referred to as a blister, may be coupled to the barrier layer 310 of the foundational flange 330. The negative-pressure source 304 may include a barrier layer and a biasing member, for example, a film layer 332, a first foam block 334, and a second foam block 335. In some embodiments, the film layer 332 may form a source flange 336 and a source cavity 338. The source cavity 338 may be a portion of the film layer 332 that is plastically deformed, such as by vacuum forming, thermoforming, micro-thermoforming, injection molding, or blow molding, for example. In some embodiments, the source cavity 338 may form walls of the negative-pressure source 304 that may be resilient or flexible. The source flange 336 may be a portion of the film layer 332 adjacent to and surrounding an opening of the source cavity 338. In some embodiments, the first foam block 334 and the second foam block 335 may be disposed in the source cavity 338. For example, the first foam block 334 and the second foam block 335 may be stacked over one another and positioned within the source cavity 338. The source flange 336 may be coupled to the barrier layer 310 of the foundational flange 330 to seal the first foam block 334 and the second foam block 335 in the source cavity 338. In some embodiments, the source flange 336 may be coupled to the barrier layer 310 by high frequency welding, ultrasonic welding, heat welding, or impulse welding, for example. In other exemplary embodiments, the source flange 336 may be coupled to the barrier layer 310 by bonding or folding, for example. In some embodiments, if the source flange 336 is coupled to the barrier layer 310 of the foundational flange 330, the source cavity 338 may be fluidly isolated from the ambient environment and the pouch 305.

The film layer 332 may be constructed from a material that can provide a fluid seal between two components or two environments, such as between the source cavity 238 and a local external environment, while allowing for repeated elastic deformation of the film layer 332. The film layer 332 may be, for example, an elastomeric film or membrane that can provide a seal between the source cavity 338 and the ambient environment. In some example embodiments, the film layer 332 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In an exemplary embodiment, the film layer 332 may be a polyurethane having a thickness between about 50 microns and about 250 microns and preferably about 100 microns.

The first foam block 334 and the second foam block 335 may have similar dimensions. For example, if the first foam block 334 and the second foam block 335 are cylindrical, the first foam block 334 and the second foam block 335 may have similar diameters. The first foam block 334 and the second foam block 335 may be a foam having a plurality of interconnected flow channels. For example, cellular foam, open-cell foam, reticulated foam, porous tissue collections, and other porous material that generally include pores, edges, and/or walls adapted to form interconnected fluid pathways. Liquids, gels, and other foams may also include or be cured to include apertures and flow channels. In some illustrative embodiments, the first foam block 334 and the second foam block 335 may be a porous foam material having interconnected cells or pores adapted to uniformly (or quasi-uniformly) distribute fluid throughout the first foam block 334 and the second foam block 335. The foam material may be either hydrophobic or hydrophilic. In one non-limiting example, the first foam block 334 and the second foam block 335 may be an open-cell, reticulated polyurethane foam such as GranuFoam® dressing available from Kinetic Concepts, Inc. of San Antonio, Tex. Another exemplary embodiment of the first foam block 334 and the second foam block 335 may be Z48AA foam from FXI.

Foam materials may have an elastic modulus, which may also be referred to as a foam modulus. Generally, the elastic modulus of a material may measure the resistance of the material to elastic deformation under a load. The elastic modulus of a material may be defined as the slope of a stress-strain curve in the elastic deformation region of the curve. The elastic deformation region of a stress-strain curve represents that portion of the curve where the deformation of the material due to the applied load is elastic, that is, not permanent. If the load is removed, the material may return to its pre-loaded state. Stiffer materials may have a higher elastic modulus, and more compliant materials may have a lower elastic modulus. Generally, references to the elastic modulus of a material refers to a material under tension.

For foam materials under compression, the elastic modulus can compared between materials by comparing the compression force deflection (CFD) of the materials. Typically, CFD is determined experimentally by compressing a sample of a material until the sample is reduced to about 25% of its uncompressed size. The load applied to reach the 25% compression of the sample is then divided by the area of the sample over which the load is applied to arrive at the CFD. The CFD can also be measured by compressing a sample of a material to about 50% of the sample's uncompressed size. The CFD of a foam material can be a function of compression level, polymer stiffness, cell structure, foam density, and cell pore size. In some embodiments, the first foam block 334 and the second foam block 335 may have a CFD that is greater than a CFD of the tissue interface 108. For example, the tissue interface 108 may have a 25% CFD of about 2 kPa. The tissue interface 108 may compress to about 25% of its uncompressed size if a load of about 2 kPa is applied to the tissue interface 108. The first foam block 334 and the second foam block 335 may have a CFD of about 4 kPA. The first foam block 334 and the second foam block 335 may compress to about 25% of its uncompressed size if a load of about 4 kPa is applied to the first foam block 334 and the second foam block 335. Thus, the first foam block 334 and the second foam block 335 is more resistant to deformation than the tissue interface 108.

Furthermore, CFD can represent the tendency of a foam to return to its uncompressed state if a load is applied to compress the foam. For example, a foam having a CFD of about 4 kPa may exert about 4 kPa in reaction to 25% compression. The CFD of the first foam block 334 and the second foam block 335 may represent the ability of the first foam block 334 and the second foam block 335 to bias the film layer 332 toward an expanded position. For example, if the first foam block 334 and the second foam block 335 is compressed to 25% of its original size, the first foam block 334 and the second foam block 335 may exert a spring force that opposes the applied force over the area of the first foam block 334 and the second foam block 335 to which the force is applied. The reactive force may be proportional to the amount the first foam block 334 and the second foam block 335 is compressed.

In some embodiments, the first foam block 334 and the second foam block 335 may have different foam moduli. For example, the first foam block 334 may have a first CFD so that the first foam block 334 may exert a first force when in the compressed state that decreases as the first foam block 334 extends to the uncompressed state. Similarly, the second foam block 335 may have a second CFD so that the second foam block 335 may exert a second force when in the compressed state that decreases as the second foam block 335 extends to the uncompressed state. If the first foam block 334 and the second foam block 335 are stacked, the first force and the second force may be combined to reach a total desired spring force. In some embodiments, the CFD of the first foam block 334 and the CFD of the second foam block 335 may be selected so that the total desired spring force for the combined first foam block 334 and the second foam block 335 is generally the same approaching the extended state as in the compressed state. For example, the first foam block 334 and the second foam block 335 may be selected so that the collective blocks exert the same upward force over the entire extension of both the first foam block 334 and the second foam block 335.

The foam material of the first foam block 334 and the second foam block 335 may be selected based on an expected volume of the pouch 305 and the tissue interface 108 (if used). The volume of the pouch 305 may define a volume of fluid to be withdrawn from the pouch 305 to achieve a therapy pressure. For example, if the pouch 305 has a volume of about 50 cubic centimeters, and no tissue interface 108 is used, removing about 10 cubic centimeters of fluid from the pouch 305 may generate a negative pressure of about 125 mm Hg. To generate 125 mm Hg with a single compression of a single foam block having a volume of 10 cm$^3$ the CFD of the single foam block may be around 17 kPa. Similarly, the moduli of the first foam block 334 and the second foam block 335 may be selected to have a combined foam modulus of about 17 kPa. Having the first foam block 334 and the second foam block 335 may allow for selection of two foams having lower than 17 kPa moduli, which may each be more easily compressed than a single foam having the 17 kPa modulus.

The first foam block 334 and the second foam block 335 may have a free volume. The free volume of first foam block 334 and the second foam block 335 may be the volume of free space of the first foam block 334 and the second foam block 335, for example, the volume of the plurality of channels of the first foam block 334 and the second foam block 335. In some embodiments, the free volume of the first foam block 334 and the second foam block 335 may be greater than the free volume of the pouch 305. For example, if the free volume of the pouch 305 is 10 cm$^3$, then the free volume of the first foam block 334 and the second foam block 335 may be greater than about 20 cm$^3$.

In some embodiments, the negative-pressure source 304 may be fluidly coupled to the cavity 311 through a fluid inlet, such as a tube 340. The tube 340 may be representative of a fluid communication path between the negative-pressure source 304 and the cavity 311. In other embodiments, the tube 340 may be a sealed channel or other fluid pathway. The tube 340 may include a lumen 342 fluidly coupled to the source cavity 338 and the pouch 305. In some embodiments, a valve, such as a check valve 344, may be fluidly coupled to the lumen 342. Exemplary check valves 344 may include ball check valves, diaphragm check valves, swing check valves, stop-check valves, duckbill valves, or pneumatic non-return valves. The check valve 344 may permit fluid communication from the pouch 305 to the source cavity 338 and prevent fluid communication from the source cavity 338 to the pouch 305. For example, if a pressure in the pouch 305 is greater than a pressure in the source cavity 338, the check valve 344 may open, and if the pressure in the source cavity 338 is greater than the pressure in the pouch 305, the check valve 344 may close. In some embodiments, a filter may be disposed on an end of the tube 340. The filter may be a hydrophobic porous polymer filter having gel blocking properties.

The source cavity 338 may also be fluidly coupled to the ambient environment through a fluid outlet, such as a tube 346. For example, the tube 346 having a lumen 348 may fluidly couple the source cavity 338 to the ambient environment. The tube 346 may be representative of a fluid communication path between the ambient environment and the source cavity 338. A valve, such as a check valve 350, may be fluidly coupled to the lumen 348 to control fluid communication through the lumen 348. Exemplary check valves 350 may include ball check valves, diaphragm check valves, swing check valves, stop-check valves, duckbill valves, or pneumatic non-return valves. In some embodiments, the check valve 350 may permit fluid communication from the source cavity 338 to the ambient environment and prevent fluid communication from the ambient environment to the source cavity 338. For example, if a pressure in the source cavity 338 is greater than a pressure in the ambient environment, the check valve 350 may open, and if the pressure in the ambient environment is greater than the pressure in the source cavity 338, the check valve 350 may close. In some embodiments, a filter may be disposed on an end of the tube 346. The filter may be a hydrophobic porous polymer filter having gel blocking properties.

The dressing assembly 302 may be disposed over the tissue site to form the sealed therapeutic environment. In some embodiments, the pouch 305 of the dressing assembly 302 may be positioned over the tissue site and the negative-pressure source 304 may be positioned over undamaged tissue proximate the tissue interface 108. A force, such as hand pressure, may be applied to the sealing flange 331 and the foundational flange 330, urging the bonding adhesive of the bonding adhesive layer 312 through the apertures 318 of the sealing adhesive layer 314 to form bonding couplings and securing the negative-pressure therapy system 300 to the tissue site.

Figure 6:
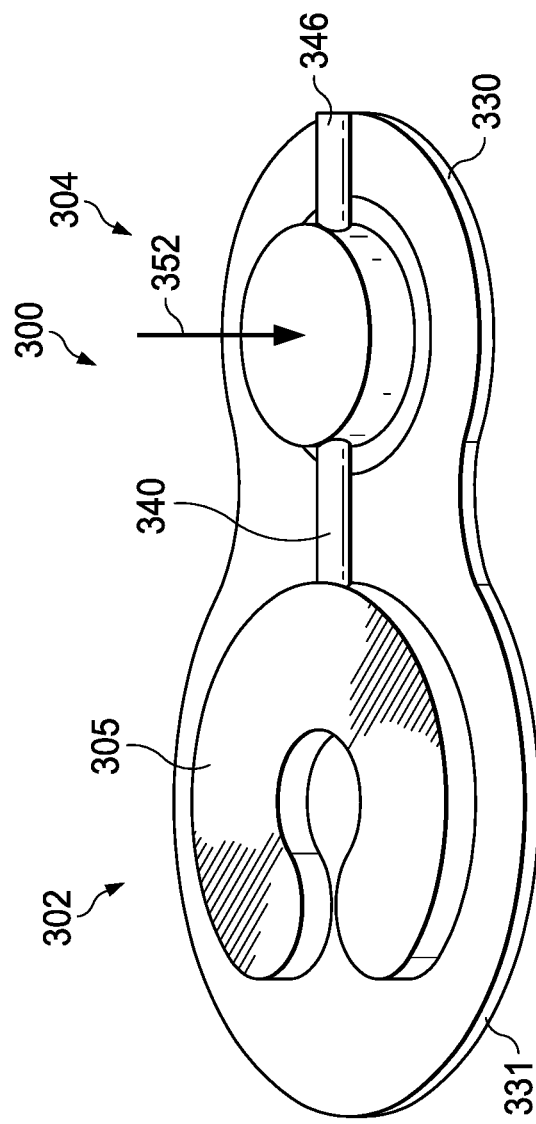
FIG. 6 is a top perspective view illustrating additional details that may be associated with an example embodiment of the negative-pressure therapy system of FIG. 5 in a first position.
Figure 7:
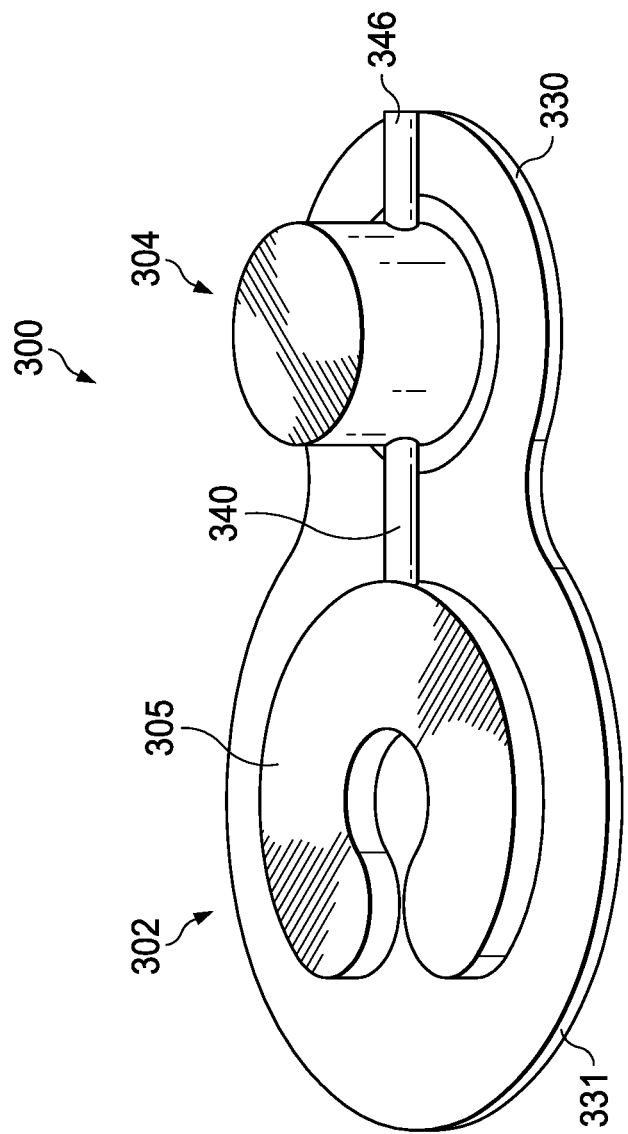
FIG. 7 is a top perspective view illustrating additional details that may be associated with an example embodiment of the negative-pressure therapy system of FIG. 5 in a second position.

FIG. 6 is a perspective view illustrating additional details of the negative-pressure source 304 in a first position, and FIG. 7 is a perspective view illustrating additional details of the negative-pressure source 304 is a second position. Once positioned, the negative-pressure source 304 may be operated to generate a negative pressure in the pouch 305. As shown in FIG. 6, a force 352, such as hand pressure, may be applied to the film layer 332 over the first foam block 334 to compress the first foam block 334 to the first position and decrease the volume of the source cavity 338. If the first foam block 334 and the source cavity 338 are fluidly isolated from the ambient environment, compression of the first foam block 334 may increase the pressure in the source cavity 338. An increase of pressure in the source cavity 338 may create a pressure differential across the check valve 344 that urges the check valve 344 to close. Similarly, an increase of pressure in the source cavity 338 may create a pressure differential across the check valve 350 that urges the check valve 350 to open, allowing fluid from the source cavity 338 to flow through the tube 346 to the ambient environment. If the force 352 is removed, the first foam block 334 may expand, increasing the volume of the source cavity 338 and decreasing the pressure in the source cavity 338. In response, the decrease in pressure in the source cavity 338 may create a pressure differential across the check valve 350 that urges the check valve 350 to close, preventing fluid from flowing from the ambient environment to the source cavity 338. The decrease in pressure in the source cavity 338 may also create a pressure differential across the check valve 344 that urges the check valve 344 to open, permitting fluid flow from the pouch 305 to the source cavity 338. Fluid may flow from the pouch 305 to the source cavity 338 until the source cavity 338 and the first foam block 334 reach their respective uncompressed positions as shown in FIG. 7. In this manner, a portion of the total volume of fluid in the sealed therapeutic environment may be removed. In response to the removal of a portion of the fluid, a smaller volume of fluid occupies the sealed therapeutic environment, decreasing the pressure. Each time the first foam block 334 is compressed and allowed to rebound, additional fluid may be removed from the sealed therapeutic environment, further decreasing the pressure.

Decreasing the pressure in the source cavity 338, the cavity 311, and the cavity between the pouch 305 and the tissue site may create a pressure differential across the dressing assembly 302. If the pressure in the source cavity 338, the cavity 311, and the cavity between the pouch 305 and the tissue site reaches the therapy pressure for negative-pressure therapy, the CFD of the first foam block 334 may be insufficient to cause the first foam block 334 to expand following compression of the first foam block 334 from the second position of FIG. 7 to the first position of FIG. 6. The therapy pressure may be the pressure at which negative-pressure therapy may be performed. In some embodiments, the therapy pressure provided by the first foam block 334 may be about 70 mm Hg of negative pressure. In other embodiments, the therapy pressure provided by the first foam block 334 may be between about 50 mm Hg and 150 mm Hg of negative pressure. If the first foam block 334 remains compressed as shown in FIG. 6, a patient or clinician may have an indication that the therapy pressure has been reached. The compressed first foam block 334 may also act as a pressure reservoir. As negative-pressure therapy is provided, there may be a natural leakage or decline of negative pressure at the tissue site. As the negative pressure decreases in the cavity 311, the source cavity 338, and the cavity between the pouch 305 and the tissue site, the pressure differential across the dressing assembly 302 may decrease and the first foam block 334 may gradually expand, reapplying negative pressure at the tissue site. In some embodiments, the negative-pressure source 304 having the first foam block 334 may maintain a therapeutic negative pressure for about 8 hours or more.

Figure 8:
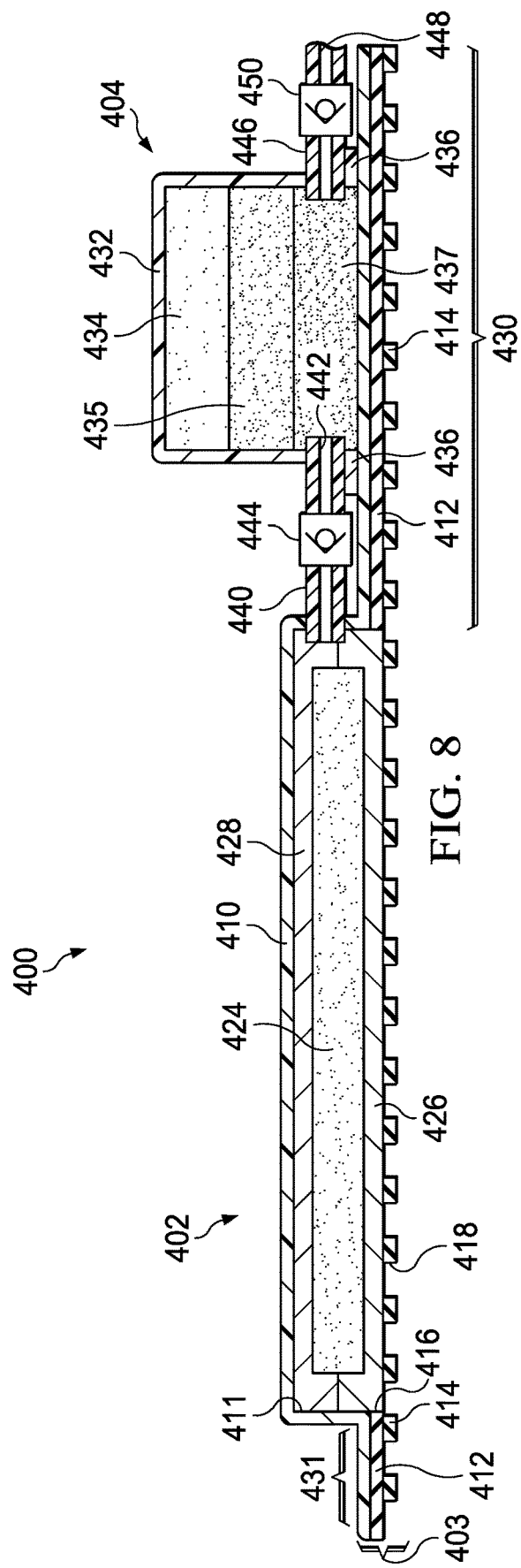
FIG. 8 is a sectional view of an example embodiment of another negative-pressure therapy system that can provide negative-pressure therapy in accordance with this specification.

FIG. 8 is a sectional view of an example embodiment of a negative-pressure therapy system 400 that can provide negative-pressure therapy in accordance with this specification. The negative-pressure therapy system 400 may be similar to and operate as described above with respect to the negative-pressure therapy system 100. Similar elements have similar reference numbers indexed to 400. As shown in FIG. 8, the negative-pressure therapy system 400 can include a dressing assembly 402 having a cover 403, a pouch 405, and a negative-pressure source 404. The cover 403, the pouch 405, and the negative-pressure source 404 may be coupled to each other. In some embodiments, the negative-pressure therapy system 400 can also include the tissue interface 108.

The pouch 405 may include an absorbent 424, a first outer layer, such as an upstream layer 426, and a second outer layer, such as a downstream layer 428. The upstream layer 426 and the downstream layer 428 may envelop or enclose the absorbent 424. The absorbent 424 may hold, stabilize, and/or solidify fluids that may be collected from the tissue site. The absorbent 424 may be formed from materials referred to as "hydrogels," "super-absorbents," or "hydrocolloids." If disposed within the dressing assembly 402, the absorbent 424 may be formed into fibers or spheres to manifold negative pressure until the absorbent 424 becomes saturated. Spaces or voids between the fibers or spheres may allow a negative pressure that is supplied to the dressing assembly 402 to be transferred within and through the absorbent 424 to the tissue site. In some exemplary embodiments, the absorbent 424 may be Texsus FP2325 having a material density of about 800 grams per square meter (gsm). In other exemplary embodiments, the absorbent material may be BASF 402C, Technical Absorbents 2317 available from Technical Absorbents (www.techabsorbents.com), sodium polyacrylate super absorbers, cellulosics (carboxy methyl cellulose and salts such as sodium CMC), or alginates.

In some exemplary embodiments, the absorbent 424 may be formed of granular absorbent components that may be scatter coated onto a paper substrate. Scatter coating involves spreading a granular absorbent powder uniformly onto a textile substrate, such as paper. The substrate, having the granular absorbent powder disposed thereon, may be passed through an oven to cure the powder and cause the powder to adhere to the paper substrate. The cured granular absorbent powder and substrate may be passed through a calender machine to provide a smooth uniform surface to the absorbent material.

In some exemplary embodiments, the upstream layer 426 and the downstream layer 428 have perimeter dimensions that may be larger than the perimeter dimensions of the absorbent 424 so that, if the absorbent 424 is positioned between the upstream layer 426 and the downstream layer 428 and the center portions of the absorbent 424, the upstream layer 426, and the downstream layer 428 are aligned, the upstream layer 426 and the downstream layer 428 may extend beyond the perimeter of the absorbent 424. In some exemplary embodiments, the upstream layer 426 and the downstream layer 428 may surround the absorbent 424. Peripheral portions of the upstream layer 426 and the downstream layer 428 may be coupled so that the upstream layer 426 and the downstream layer 428 enclose the absorbent 424. The upstream layer 426 and the downstream layer 428 may be coupled by high frequency welding, ultrasonic welding, heat welding, or impulse welding, for example. In other exemplary embodiments, the upstream layer 426 and the downstream layer 428 may be coupled by bonding or folding, for example.

The upstream layer 426 may be formed of non-woven material in some embodiments. For example, the upstream layer 426 may have a polyester fibrous porous structure. The upstream layer 426 may be porous, but preferably the upstream layer 426 is not perforated. The upstream layer 426 may have a material density between about 80 gsm and about 150 gsm. In other exemplary embodiments, the material density may be lower or greater depending on the particular application of the pouch 405. The upstream layer 426 may be formed of Libeltex TDL2, for example. In other embodiments, the upstream layer 426 may be formed of Libeltex TL4. The upstream layer 426 may have a hydrophilic side and a hydrophobic side.

The downstream layer 428 may also be formed of a non-woven material in some embodiments. For example, the downstream layer 428 may have a polyester fibrous porous structure. The downstream layer 428 may be porous, but the downstream layer 428 preferably is not perforated. The downstream layer 428 may have a material density between about 80 gsm and about 150 gsm. In other exemplary embodiments, the material density may be lower or greater depending on the particular application of the pouch 405. The material density of the downstream layer 428 may be greater or less than the material density of the upstream layer 426. In some embodiments, a thickness of the downstream layer 428 may be greater than a thickness of the upstream layer 426. In other embodiments, the thickness of the downstream layer 428 may be less than the thickness of the upstream layer 426. The downstream layer 428 may be formed of Libeltex TL4. In other exemplary embodiments, the downstream layer 428 may be formed of Libeltex TDL2.

The upstream layer 426 and the downstream layer 428 may be manifolding layers configured to facilitate fluid movement through the pouch 405. In some embodiments, the upstream layer 426 and the downstream layer 428 may each have a hydrophobic side and a hydrophilic side. The hydrophobic side may also be referred to as a wicking side, wicking surface, distribution surface, distribution side, or fluid distribution surface. The hydrophobic side may be a smooth distribution surface configured to move fluid along a grain of the upstream layer 426 and the downstream layer 428, distributing fluid throughout the upstream layer 426 and the downstream layer 428. The hydrophilic side may be configured to acquire bodily fluid from the hydrophobic side to aid in bodily fluid movement into the absorbent 424. The hydrophilic side may also be referred to as a fluid acquisition surface, fluid acquisition side, hydrophilic acquisition surface, or hydrophilic acquisition side. The hydrophilic side may be a fibrous surface and be configured to draw fluid into the upstream layer 426 and the downstream layer 428. In some embodiments, the hydrophilic side of the upstream layer 426 and the downstream layer 428 may be positioned adjacent to the absorbent 424. In other embodiments, the hydrophobic side of the upstream layer 426 and the downstream layer 428 may be positioned adjacent to the absorbent 424. In still other embodiments, the hydrophilic side of one of the upstream layer 426 or the downstream layer 428 may be positioned adjacent to the absorbent 424, and the hydrophobic side of the other of the upstream layer 426 or the downstream layer 428 may be positioned adjacent to the absorbent 424.

In some embodiments, the cover 403 may include or may be a hybrid drape that includes a barrier layer 410, a bonding adhesive layer 412, and a sealing adhesive layer 414. The barrier layer 410 may be formed from a range of medically approved films ranging in thickness from about 15 microns (μm) to about 50 microns (μm). The barrier layer 410 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the barrier layer 410 may be formed from a breathable cast matt polyurethane film sold by Expopack Advanced Coatings of Wrexham, United Kingdom, under the name INSPIRE 2301.

The barrier layer 410 may have a high moisture vapor transmission rate (MVTR). The MVTR of the barrier layer 410 allows vapor to egress and inhibits liquids from exiting. In some embodiments, the MVTR of the barrier layer 410 may be greater than or equal to 300 g/m$^2$/24 hours. In other embodiments, the MVTR of the barrier layer 410 may be greater than or equal to 1000 g/m$^2$/24 hours. The illustrative INSPIRE 2301 film may have an MVTR (inverted cup technique) of 14400 g/m$^2$/24 hours and may be approximately 30 microns thick. In other embodiments, a drape having a low MVTR or that allows no vapor transfer might be used. The barrier layer 410 can also function as a barrier to liquids and microorganisms.

In some embodiments, the barrier layer 410 may be adapted to form a bulge on a first side of the barrier layer 410 and a cavity 411 on an opposite side of the barrier layer 410. For example, the barrier layer 410 may be placed on a mold and stretched to plastically deform a portion of the barrier layer 410, forming the cavity 411. A periphery of the barrier layer 410 that is not stretched by the formation of the cavity 411 may form a flange surrounding the cavity 411. In some embodiments, the cavity 411 may be positioned so that a portion of the flange may be larger on a first side of the cavity 411 than on a second side of the cavity 411. The disparity in sizes of the flange may form a foundational flange 430 and a sealing flange 431. In some embodiments, the pouch 405 may be disposed in the cavity 411. The cavity 411 may also be a portion of the barrier layer 410 that is free of the bonding adhesive layer 412. For example, during manufacturing, a portion of the barrier layer 410 may be left without the bonding adhesive layer 412; the area of the barrier layer 410 without the bonding adhesive layer 412 may be equal to a surface area of the pouch 405 to be covered by the barrier layer 410.

The foundational flange 430 may extend away from the cavity 411. In some embodiments, the foundational flange 430 may have a length and a width sufficient to permit other objects to be coupled to the dressing assembly 402. In some embodiments, the foundational flange 430 may support the negative-pressure source 404, as illustrated in FIG. 8.

The bonding adhesive layer 412 may be coupled to the barrier layer 410 on a side of the barrier layer 410 having an opening of the cavity 411. In some embodiments, the bonding adhesive layer 412 may include an aperture 416. The aperture 416 may be coextensive with the opening of the cavity 411. For example, the bonding adhesive layer 412 may cover the barrier layer 410 at the foundational flange 430 and the sealing flange 431, leaving the portion of the barrier layer 410 forming the cavity 411 free of the bonding adhesive layer 412.

The bonding adhesive layer 412 may comprise an acrylic adhesive, rubber adhesive, high-tack silicone adhesive, polyurethane, or other substance. In an illustrative example, the bonding adhesive layer 412 comprises an acrylic adhesive with coating weight of 15 grams/m$^2$ (gsm) to 70 grams/m$^2$ (gsm). The bonding adhesive layer 412 may be a continuous layer of material or may be a layer with apertures (not shown). The apertures may be formed after application of the bonding adhesive layer 412 or may be formed by coating the bonding adhesive layer 412 in patterns on a carrier layer. In some embodiments, the bond strength of the bonding adhesive may have a peel adhesion or resistance to being peeled from a stainless steel material between about 6N/25 mm to about 40N/25 mm on stainless steel substrate at 23° C. at 50% relative humidity based on the American Society for Testing and Materials ("ASTM") standard ASTM D3330. The bonding adhesive layer 412 may be about 30 microns to about 60 microns in thickness.

The sealing adhesive layer 414 may be coupled to the bonding adhesive layer 412 and the pouch 405. For example, the sealing adhesive layer 414 may cover the sealing flange 431, the pouch 405, and the foundational flange 430. The sealing adhesive layer 414 may be formed with the plurality of apertures 418. The apertures 418 may be numerous shapes, for example, circles, squares, stars, ovals, polygons, slits, complex curves, rectilinear shapes, triangles, or other shapes. Each aperture 418 of the plurality of apertures 418 may have an effective diameter, which is the diameter of a circular area having the same surface area as the aperture 418. The average effective diameter of each aperture 418 may typically be in the range of about 6 mm to about 50 mm. The plurality of apertures 418 may have a uniform pattern or may be randomly distributed in the sealing adhesive layer 414. Generally, the apertures 418 may be disposed across a length and width of the sealing adhesive layer 414.

The sealing adhesive layer 414 may comprise a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 40 gsm-70 gsm acrylic), polyurethane, polyolefin, or hydrogenated styrenic copolymers. The sealing adhesive layer 414 may have a thickness in the range of about 100 microns (μm) to about 1000 microns (μm). In some embodiments, the sealing adhesive layer 414 may have stiffness between about 5 Shore OO and about 80 Shore OO. The sealing adhesive layer 414 may be hydrophobic or hydrophilic. The sealing adhesive of the sealing adhesive layer 414 may be an adhesive having a low to medium tackiness, for example, a silicone polymer, polyurethane, or an additional acrylic adhesive. In some embodiments, the bond strength of the sealing adhesive may have a peel adhesion or resistance to being peeled from a stainless steel material between about 0.5N/25 mm to about 4.5N/25 mm on stainless steel substrate at 23° C. at 50% relative humidity based on ASTM D3330. The sealing adhesive may have a tackiness such that the sealing adhesive may achieve the bond strength above after a contact time of less than 60 seconds. Tackiness may be considered a bond strength of an adhesive after a very low contact time between the adhesive and a substrate. In some embodiments, the sealing adhesive layer 414 may have a tackiness that may be about 40% to about 50% of the tackiness of the bonding adhesive of the bonding adhesive layer 412.

In the assembled state, the bonding adhesive layer 412 may be coupled to the barrier layer 410. The sealing adhesive layer 414 may be coupled to the bonding adhesive layer 412 at the sealing flange 431 and the foundational flange 430 and to the pouch 405 at the cavity 411. In some embodiments, a scrim layer may be disposed in the sealing adhesive layer 414. The scrim layer may provide additional mechanical support for the sealing adhesive layer 414. In some embodiments, the sealing adhesive layer 414 may be treated on a portion and a side of the sealing adhesive layer 414 adjacent to the pouch 405. The treated portion of the sealing adhesive layer 414 may reduce the tackiness of the sealing adhesive layer 414 so that the sealing adhesive layer 414 may not readily adhere to the pouch 405. The initial tackiness of the sealing adhesive layer 414 is preferably sufficient to initially couple the sealing adhesive layer 414 to the epidermis by forming sealing couplings. Once in the desired location, a force can be applied to the barrier layer 410 of the cover 403. For example, the user may rub the foundational flange 430 and the sealing flange 431. This action can cause at least a portion of the bonding adhesive layer 412 to be forced into the plurality of apertures 418 and into contact with the epidermis to form bonding couplings. The bonding couplings provide secure, releasable mechanical fixation to the epidermis.

The average effective diameter of the plurality of apertures 418 for the sealing adhesive layer 414 may be varied as one control of the tackiness or adhesion strength of the cover 403. In this regard, there is interplay between three main variables for each embodiment: the thickness of the sealing adhesive layer 414, the average effective diameter of the plurality of apertures 418, and the tackiness of the bonding adhesive layer 412. The more bonding adhesive of the bonding adhesive layer 412 that extends through the apertures 418, the stronger the bond of the bonding coupling. The thinner the sealing adhesive layer 414, the more bonding adhesive of the bonding adhesive layer 412 generally extends through the apertures 418 and the greater the bond of the bonding coupling. As an example of the interplay, if a very tacky bonding adhesive layer 412 is used and the thickness of the sealing adhesive layer 414 is small, the average effective diameter of the plurality of apertures 418 may be relatively smaller than apertures 418 in a thicker sealing adhesive layer 414 and a less tacky bonding adhesive layer 412. In some embodiments, the thickness of the sealing adhesive layer 414 may be approximately 200 microns, the thickness of the bonding adhesive layer 412 is approximately 30 microns with a tackiness of 2000 g/25 cm wide strip, and the average effective diameter of each aperture 418 is approximately about 6 mm.

As illustrated in FIG. 8, the negative-pressure source 404, which may also be referred to as a blister, may be coupled to the barrier layer 410 of the foundational flange 430. The negative-pressure source 404 may include a barrier layer and a biasing member, for example, a film layer 432, a first foam block 434, a second foam block 435, and a third foam block 437. In some embodiments, the film layer 432 may form a source flange 436 and a source cavity 438. The source cavity 438 may be a portion of the film layer 432 that is plastically deformed, such as by vacuum forming, thermoforming, micro-thermoforming, injection molding, or blow molding, for example. In some embodiments, the source cavity 438 may form walls of the negative-pressure source 404 that may be resilient or flexible. The source flange 436 may be a portion of the film layer 432 adjacent to and surrounding an opening of the source cavity 438. In some embodiments, the first foam block 434, the second foam block 435, and the third foam block 437 may be disposed in the source cavity 438. For example, the first foam block 434, the second foam block 435, and the third foam block 437 may be stacked over one another and positioned within the source cavity 438. The source flange 436 may be coupled to the barrier layer 410 of the foundational flange 430 to seal the first foam block 434, the second foam block 435, and the third foam block 437 in the source cavity 438. In some embodiments, the source flange 436 may be coupled to the barrier layer 410 by high frequency welding, ultrasonic welding, heat welding, or impulse welding, for example. In other exemplary embodiments, the source flange 436 may be coupled to the barrier layer 410 by bonding or folding, for example. In some embodiments, if the source flange 436 is coupled to the barrier layer 410 of the foundational flange 430, the source cavity 438 may be fluidly isolated from the ambient environment and the pouch 405.

The film layer 432 may be constructed from a material that can provide a fluid seal between two components or two environments, such as between the source cavity 438 and a local external environment, while allowing for repeated elastic deformation of the film layer 432. The film layer 432 may be, for example, an elastomeric film or membrane that can provide a seal between the source cavity 438 and the ambient environment. In some example embodiments, the film layer 432 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In an exemplary embodiment, the film layer 432 may be a polyurethane having a thickness between about 50 microns and about 250 microns and preferably about 100 microns.

The first foam block 434, the second foam block 435, and the third foam block 437 may have similar dimensions. For example, if the first foam block 434, the second foam block 435, and the third foam block 437 are cylindrical, the first foam block 434, the second foam block 435, and the third foam block 437 may have similar diameters. The first foam block 434, the second foam block 435, and the third foam block 437 may be a foam having a plurality of interconnected flow channels. For example, cellular foam, open-cell foam, reticulated foam, porous tissue collections, and other porous material that generally include pores, edges, and/or walls adapted to form interconnected fluid pathways. Liquids, gels, and other foams may also include or be cured to include apertures and flow channels. In some illustrative embodiments, the first foam block 434, the second foam block 435, and the third foam block 437 may be a porous foam material having interconnected cells or pores adapted to uniformly (or quasi-uniformly) distribute fluid throughout the first foam block 434, the second foam block 435, and the third foam block 437. The foam material may be either hydrophobic or hydrophilic. In one non-limiting example, the first foam block 434, the second foam block 435, and the third foam block 437 may be an open-cell, reticulated polyurethane foam such as GranuFoam® dressing available from Kinetic Concepts, Inc. of San Antonio, Tex. Another exemplary embodiment of the first foam block 434, the second foam block 435, and the third foam block 437 may be Z48AA foam from FXI.

Foam materials may have an elastic modulus, which may also be referred to as a foam modulus. Generally, the elastic modulus of a material may measure the resistance of the material to elastic deformation under a load. The elastic modulus of a material may be defined as the slope of a stress-strain curve in the elastic deformation region of the curve. The elastic deformation region of a stress-strain curve represents that portion of the curve where the deformation of the material due to the applied load is elastic, that is, not permanent. If the load is removed, the material may return to its pre-loaded state. Stiffer materials may have a higher elastic modulus, and more compliant materials may have a lower elastic modulus. Generally, references to the elastic modulus of a material refers to a material under tension.

For foam materials under compression, the elastic modulus can compared between materials by comparing the compression force deflection (CFD) of the materials. Typically, CFD is determined experimentally by compressing a sample of a material until the sample is reduced to about 25% of its uncompressed size. The load applied to reach the 25% compression of the sample is then divided by the area of the sample over which the load is applied to arrive at the CFD. The CFD can also be measured by compressing a sample of a material to about 50% of the sample's uncompressed size. The CFD of a foam material can be a function of compression level, polymer stiffness, cell structure, foam density, and cell pore size. The first foam block 434, the second foam block 435, and the third foam block 437 may collectively have a CFD of about 4 kPA. The first foam block 434, the second foam block 435, and the third foam block 437 may compress to about 25% of its uncompressed size if a load of about 4 kPA is applied to the first foam block 434, the second foam block 435, and the third foam block 437. Thus, the first foam block 434, the second foam block 435, and the third foam block 437 is more resistant to deformation than the tissue interface 108.

Furthermore, CFD can represent the tendency of a foam to return to its uncompressed state if a load is applied to compress the foam. For example, a foam having a CFD of about 4 kPa may exert about 4 kPa in reaction to 25% compression. The collective CFD of the first foam block 434, the second foam block 435, and the third foam block 437 may represent the ability of the first foam block 434, the second foam block 435, and the third foam block 437 to bias the film layer 432 toward an expanded position. For example, if the first foam block 434, the second foam block 435, and the third foam block 437 is compressed to 25% of its original size, the first foam block 434, the second foam block 435, and the third foam block 437 may collectively exert a spring force that opposes the applied force over the area of the first foam block 434, the second foam block 435, and the third foam block 437 to which the force is applied. The reactive force may be proportional to the amount the first foam block 434, the second foam block 435, and the third foam block 437 are compressed.

In some embodiments, the first foam block 434, the second foam block 435, and the third foam block 437 may have different foam moduli. For example, the first foam block 434 may have a first CFD so that the first foam block 434 may exert a first force when in the compressed state that decreases as the first foam block 434 extends to the uncompressed state. Similarly, the second foam block 435 may have a second CFD so that the second foam block 435 may exert a second force when in the compressed state that decreases as the second foam block 435 extends to the uncompressed state. The third foam block 437 may have a third CFD so that the third foam block 437 may exert a third force when in the compressed state that decreases as the third foam block 437 extends to the uncompressed state. If the first foam block 434, the second foam block 435, and the third foam block 437 are stacked, the first force, the second force, and the third may be combined to reach a total desired spring force. In some embodiments, the CFD of the first foam block 434, the CFD of the second foam block 435, and the CFD of the third foam block 437 may be selected so that the total desired spring force for the combined first foam block 434, the second foam block 435, and the third foam block 437 is generally the same approaching the extended state as in the compressed state. For example, the first foam block 434, the second foam block 435, and the third foam block 437 may be selected so that the collective blocks exert the same upward force over the entire extension of both the first foam block 434, the second foam block 435, and the third foam block 437.

The foam material of the first foam block 434, the second foam block 435, and the third foam block 437 may be selected based on an expected volume of the pouch 405 and the tissue interface 108 (if used). The volume of the pouch 405 may define a volume of fluid to be withdrawn from the pouch 405 to achieve a therapy pressure. For example, if the pouch 405 has a volume of about 50 cubic centimeters, and no tissue interface 108 is used, removing about 10 cubic centimeters of fluid from the pouch 405 may generate a negative pressure of about 125 mm Hg. To generate 125 mm Hg with a single compression of a single foam block having a volume of 10 cm$^3$ the CFD of the single foam block may be around 17 kPa. Similarly, the moduli of the first foam block 434, the second foam block 435, and the third foam block 437 may be selected to have a combined foam modulus of about 17 kPa. Having the first foam block 434, the second foam block 435, and the third foam block 437 may allow for selection of two foams having lower than 17 kPa moduli, which may each be more easily compressed than a single foam having the 17 kPa modulus.

The first foam block 434, the second foam block 435, and the third foam block 437 may have a free volume. The free volume of first foam block 434, the second foam block 435, and the third foam block 437 may be the volume of free space of the first foam block 434, the second foam block 435, and the third foam block 437, for example, the volume of the plurality of channels of the first foam block 434, the second foam block 435, and the third foam block 437. In some embodiments, the free volume of the first foam block 434, the second foam block 435, and the third foam block 437 may be greater than the free volume of the pouch 405. For example, if the free volume of the pouch 405 is 10 cm$^3$, then the free volume of the first foam block 434, the second foam block 435, and the third foam block 437 may be greater than about 20 cm$^3$.

In some embodiments, the negative-pressure source 404 may be fluidly coupled to the to the cavity 411 through a fluid inlet, such as a tube 440. The tube 440 may be representative of a fluid communication path between the negative-pressure source 404 and the cavity 411. In other embodiments, the tube 440 may be a sealed channel or other fluid pathway. The tube 440 may include a lumen 442 fluidly coupled to the source cavity 438 and the pouch 405. In some embodiments, a valve, such as a check valve 444, may be fluidly coupled to the lumen 442. Exemplary check valves 444 may include ball check valves, diaphragm check valves, swing check valves, stop-check valves, duckbill valves, or pneumatic non-return valves. The check valve 444 may permit fluid communication from the pouch 405 to the source cavity 438 and prevent fluid communication from the source cavity 438 to the pouch 405. For example, if a pressure in the pouch 405 is greater than a pressure in the source cavity 438, the check valve 444 may open, and if the pressure in the source cavity 438 is greater than the pressure in the pouch 405, the check valve 444 may close. In some embodiments, a filter may be disposed on an end of the tube 440. The filter may be a hydrophobic porous polymer filter having gel blocking properties.

The source cavity 438 may also be fluidly coupled to the ambient environment through a fluid outlet, such as a tube 446. For example, the tube 446 having a lumen 448 may fluidly couple the source cavity 438 to the ambient environment. The tube 446 may be representative of a fluid communication path between the ambient environment and the source cavity 438. A valve, such as a check valve 450, may be fluidly coupled to the lumen 448 to control fluid communication through the lumen 448. Exemplary check valves 450 may include ball check valves, diaphragm check valves, swing check valves, stop-check valves, duckbill valves, or pneumatic non-return valves. In some embodiments, the check valve 450 may permit fluid communication from the source cavity 438 to the ambient environment and prevent fluid communication from the ambient environment to the source cavity 438. For example, if a pressure in the source cavity 438 is greater than a pressure in the ambient environment, the check valve 450 may open, and if the pressure in the ambient environment is greater than the pressure in the source cavity 438, the check valve 450 may close. In some embodiments, a filter may be disposed on an end of the tube 446. The filter may be a hydrophobic porous polymer filter having gel blocking properties.

The dressing assembly 402 may be disposed over the tissue site to form the sealed therapeutic environment. In some embodiments, the pouch 405 of the dressing assembly 402 may be positioned over the tissue site and the negative-pressure source 404 may be positioned over undamaged tissue proximate the tissue site. A force, such as hand pressure, may be applied to the sealing flange 431 and the foundational flange 430, urging the bonding adhesive of the bonding adhesive layer 412 through the apertures 418 of the sealing adhesive layer 414 to form bonding couplings and securing the dressing assembly 402 to the tissue site.

Figure 9:
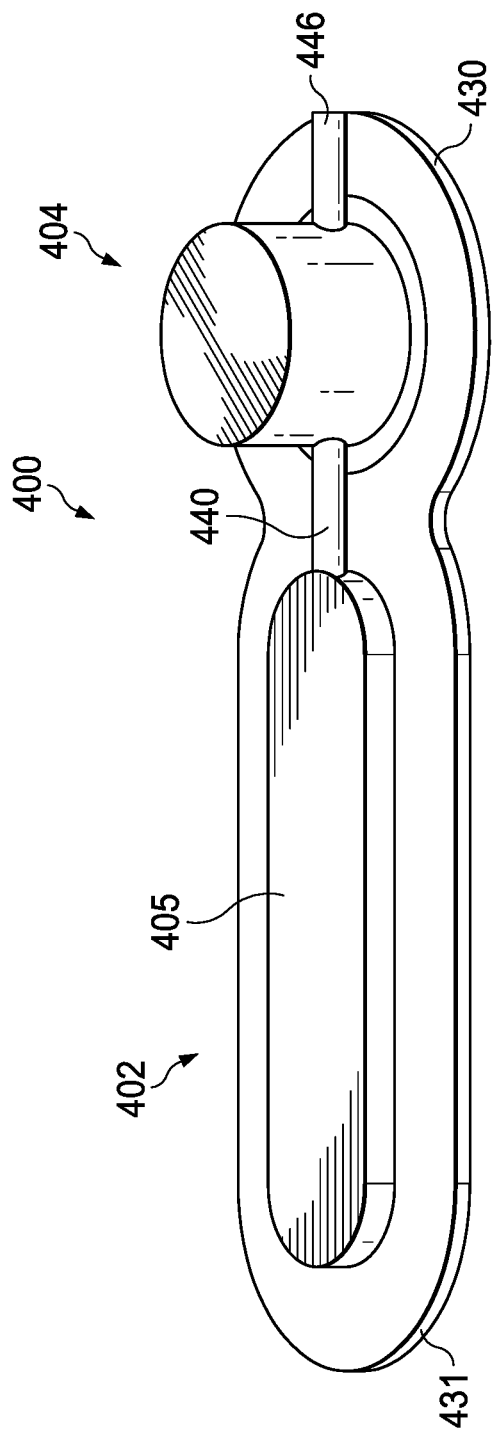
FIG. 9 is a top perspective view illustrating additional details that may be associated with an example embodiment of the negative-pressure therapy system of FIG. 8.

FIG. 9 is a perspective view illustrating additional details of the negative-pressure source 404. Once positioned, the negative-pressure source 404 may be operated to generate a negative pressure in the pouch 405. A force, such as hand pressure, may be applied to the film layer 432 over the first foam block 434, the second foam block 435, and the third foam block 437 to compress the first foam block 434, the second foam block 435, and the third foam block 437 to decrease the volume of the source cavity 438. If the first foam block 434, the second foam block 435, and the third foam block 437 and the source cavity 438 are fluidly isolated from the ambient environment, compression of the first foam block 434, the second foam block 435, and the third foam block 437 may increase the pressure in the source cavity 438. An increase of pressure in the source cavity 438 may create a pressure differential across the check valve 444 that urges the check valve 444 to close. Similarly, an increase of pressure in the source cavity 438 may create a pressure differential across the check valve 450 that urges the check valve 450 to open, allowing fluid from the source cavity 438 to flow through the tube 446 to the ambient environment. If the force is removed, the first foam block 434, the second foam block 435, and the third foam block 437 may expand, increasing the volume of the source cavity 438 and decreasing the pressure in the source cavity 438. In response, the decrease in pressure in the source cavity 438 may create a pressure differential across the check valve 450 that urges the check valve 450 to close, preventing fluid from flowing from the ambient environment to the source cavity 438. The decrease in pressure in the source cavity 438 may also create a pressure differential across the check valve 444 that urges the check valve 444 to open, permitting fluid flow from the pouch 405 to the source cavity 438. Fluid may flow from the pouch 405 to the source cavity 438 until the source cavity 438 and the first foam block 434, the second foam block 435, and the third foam block 437 reach their respective uncompressed positions. In this manner, a portion of the total volume of fluid in the sealed therapeutic environment may be removed. In response to the removal of a portion of the fluid, a smaller volume of fluid occupies the sealed therapeutic environment, decreasing the pressure. Each time the first foam block 434, the second foam block 435, and the third foam block 437 are compressed and allowed to rebound, additional fluid may be removed from the sealed therapeutic environment, further decreasing the pressure.

Decreasing the pressure in the sealed therapeutic environment may create a pressure differential across the dressing assembly 402. If the pressure in the sealed therapeutic environment reaches the therapy pressure for negative-pressure therapy, the CFD of the first foam block 434, the second foam block 435, and the third foam block 437 may be insufficient to cause the first foam block 434, the second foam block 435, and the third foam block 437 to expand following compression of the first foam block 434, the second foam block 435, and the third foam block 437. The therapy pressure may be the pressure at which negative-pressure therapy may be performed. In some embodiments, the therapy pressure provided by the first foam block 434, the second foam block 435, and the third foam block 437 may be about 70 mm Hg of negative pressure. In other embodiments, the therapy pressure provided by the first foam block 434, the second foam block 435, and the third foam block 437 may be between about 50 mm Hg and 150 mm Hg of negative pressure. If the first foam block 434, the second foam block 435, and the third foam block 437 remains compressed, a patient or clinician may have an indication that the therapy pressure has been reached. The compressed first foam block 434, the second foam block 435, and the third foam block 437 may also act as a pressure reservoir. As negative-pressure therapy is provided, there may be a natural leakage or decline of negative pressure at the tissue site. As the negative pressure decreases in the sealed therapeutic environment, the pressure differential across the dressing assembly 402 may decrease and the first foam block 434, the second foam block 435, and the third foam block 437 may gradually expand, reapplying negative pressure at the tissue site. In some embodiments, the negative-pressure source 404 having the first foam block 434, the second foam block 435, and the third foam block 437 may maintain a therapeutic negative pressure for about 8 hours or more.

In some embodiments, the fluid container and dressing assembly may be shaped to accommodate differently shaped tissue sites. For example, the pouch 105 and the dressing assembly 102 of FIGS. 1-3 and the pouch 205 and the dressing assembly 202 of FIG. 4 may have a square shape and a large area to accommodate a tissue site having a large area. The pouch 305 and the dressing assembly 302 of FIG. 5, FIG. 6, and FIG. 7 may have a curved shape to accommodate wounds having a significant curvature or that may be located on or near an articulating joint. The pouch 405 and the dressing assembly 402 of FIG. 8 and FIG. 9 may have a rectangular shape to accommodate a tissue site, such as a linear wound, that has a high length to width ratio.

In some embodiments, the foam block 134, 234, 334, 335, 434, 435, 437 may be replaced with other types of elastic elements, such a polymer coil spring formed of polyurethane or acrylonitrile butadiene styrene (ABS). In some embodiments, the negative-pressure source 104, 204, 304, and 404 may comprise or may be a blow-molded bellows that is coupled to the foundational flange 130, 230, 330, or 430.

While shown in a few illustrative embodiments, a person having ordinary skill in the art will recognized that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for providing negative-pressure therapy to a tissue site, the system comprising:
    an absorbent;
    a sealing layer configured to cover the absorbent, the sealing layer having a periphery extending beyond an edge of the absorbent;
    a blister having flexible walls and fluidly coupled to the absorbent, the blister having a collapsed position and an expanded position, the blister coupled to a top portion of the periphery of the sealing layer;
    a foam block disposed in the blister, the foam block having a compressive force deflection greater than a compressive force deflection of a tissue interface configured to be positioned between the tissue site and the absorbent;
    a first conduit configured to fluidly couple the blister to the absorbent;
    a second conduit configured to fluidly couple the blister to the ambient environment;
    a first check valve disposed in the first conduit and configured to prevent fluid flow from the blister into the absorbent if the blister is moved from the expanded position to the collapsed position; and
    a second check valve disposed in the second conduit and configured to prevent fluid flow from the ambient environment into the blister if the blister is moved from the collapsed position to the expanded position.

2. The system of claim 1, wherein:
    the absorbent is coupled to the sealing layer; and
    the first conduit fluidly couples the absorbent to the blister through the sealing layer.

3. The system of claim 1, wherein the periphery of the sealing layer further comprises:
    a barrier layer;
    a bonding adhesive layer coupled to the barrier layer; and
    a sealing adhesive layer having a plurality of apertures and coupled to the barrier layer, the bonding adhesive layer configured to extend at least partially through the plurality of apertures in the sealing adhesive layer in response to force applied to the barrier layer.

4. The system of claim 3, wherein the bonding adhesive layer and the sealing adhesive layer are registered with each other.

5. The system of claim 3, wherein the sealing adhesive layer is coupled to the bonding adhesive layer.

6. The system of claim 1, further comprising a filter disposed in a fluid path between the first check valve and the blister.

7. The system of claim 6, wherein the filter comprises a hydrophobic porous polymer.

8. The system of claim 6, wherein the filter includes gel-blocking properties.

9. The system of claim 1, wherein the blister has a larger volume than a combined volume of the absorbent and the tissue interface.

10. The system of claim 1, further comprising an upstream layer and a downstream layer, the absorbent configured to be positioned between the upstream layer and the downstream layer.

11. The system of claim 10, wherein the upstream layer and the downstream layer each have a hydrophobic side and a hydrophilic side, wherein the hydrophilic side is configured to acquire fluid from the hydrophobic side and assist in moving the fluid into the absorbent.

12. The system of claim 1, wherein the periphery of the sealing layer forms a foundational flange on a first side of the absorbent and a sealing flange on a second side of the absorbent.

13. The system of claim 12, wherein the blister comprises a film layer configured to be coupled to the foundational flange and form a source cavity, the foam block configured to be disposed in the source cavity.

14. The system of claim 13, wherein the film layer comprises a source flange configured to couple the film layer to the foundational flange.

15. A method for providing negative-pressure therapy to a tissue site, the method comprising:
positioning a dressing assembly adjacent to the tissue site, the dressing assembly having:
an absorbent;
a sealing layer configured to cover the absorbent, the sealing layer having a periphery extending beyond an edge of the absorbent;
a blister fluidly coupled to the absorbent, the blister having a collapsed position and an expanded position, the blister comprising a source cavity and a foam block disposed in the source cavity, the foam block configured to bias the blister, the blister coupled to a top portion of the periphery of the sealing layer;
wherein the foam block has a compressive force deflection greater than a compressive force deflection of a tissue interface configured to be positioned between the tissue site and the sealing layer;
a first tube configured to fluidly couple the blister to the absorbent;
a second tube configured to fluidly couple the blister to the ambient environment;
a first check valve disposed in the first tube and configured to prevent fluid flow from the blister into the absorbent if the blister is moved from the expanded position to the collapsed position; and
a second check valve disposed in the second tube and configured to prevent fluid flow from the ambient environment into the blister if the blister is moved from the collapsed position to the expanded position;
collapsing the blister from the expanded position to the collapsed position to evacuate the blister; and
expanding the blister from the collapsed position to the expanded position to draw fluid from the absorbent.

16. The method of claim 15, further comprising indicating that a pressure at the absorbent is about a therapy pressure.

17. The method of claim 16, wherein indicating that a pressure at the absorbent is about the therapy pressure comprises:
collapsing the blister from the expanded position to the collapsed position to evacuate the blister; and
maintaining the blister in the collapsed position.

* * * * *